(12) United States Patent
Tohma et al.

(10) Patent No.: US 7,826,978 B2
(45) Date of Patent: Nov. 2, 2010

(54) BLOOD IMAGE ANALYZER

(75) Inventors: Ryuichi Tohma, Akashi (JP); Yasuo Yonekura, Kobe (JP); Hiroyuki Tanaka, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 399 days.

(21) Appl. No.: 11/998,219

(22) Filed: Nov. 29, 2007

(65) Prior Publication Data

US 2008/0201082 A1   Aug. 21, 2008

(30) Foreign Application Priority Data

Nov. 30, 2006   (JP)   .............................. 2006-324457

(51) Int. Cl.
*G06F 19/00* (2006.01)
(52) U.S. Cl. ....................................................... 702/19
(58) Field of Classification Search ................... 702/19, 702/23, 182–185
See application file for complete search history.

(56) References Cited

U.S. PATENT DOCUMENTS

2008/0006535 A1 * 1/2008 Paik et al. .................... 204/600

FOREIGN PATENT DOCUMENTS

JP   H11-083726   3/1999

* cited by examiner

*Primary Examiner*—Edward Raymond
(74) *Attorney, Agent, or Firm*—Brinks Hofer Gilson & Lione

(57) ABSTRACT

A blood image analyzer is disclosed that comprising: an image capturing unit for capturing a blood image of a sample; an analyzing part for analyzing the sample based on the blood image; an identification information reader for reading, from the sample, identification information assigned to the sample; a transportation part for transporting the sample to the identification information reader and the image capturing unit; a first detector for detecting the sample at a first detection position on a pathway of the sample transported by the transportation part; a display; and a controller for controlling the display, so as to display, based on a detection result by the first detector, a screen including a first identification information display region, wherein the first identification information display region displays identification information of the sample being at the first detection position.

23 Claims, 16 Drawing Sheets

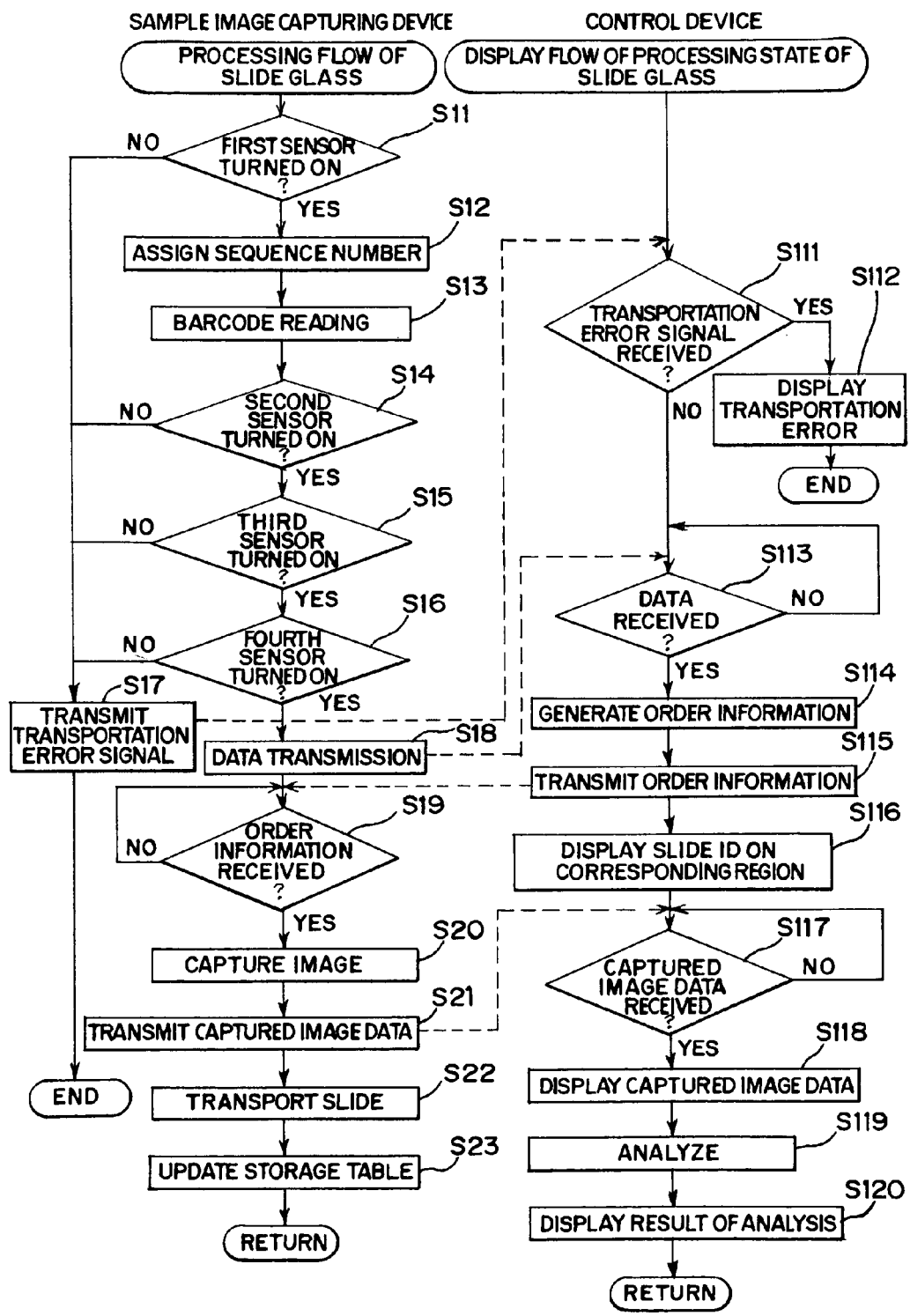

Fig. 19

| Sensor number | Sequence number |
|---|---|
| First sensor | 000006 |
| Second sensor | 000005 |
| Third sensor | 000004 |
| Fourth sensor | 000003 |
| Storing part number | |
| First storing part | 000002 |
| Second storing part | 000001 |
| Third storing part | |
| ⋮ | ⋮ |
| Twenty fifth storing part | |

Fig. 20

| Sensor number | Sequence number |
|---|---|
| First sensor | |
| Second sensor | 000006 |
| Third sensor | 000005 |
| Fourth sensor | 000004 |
| Storing part number | |
| First storing part | 000003 |
| Second storing part | 000002 |
| Third storing part | 000001 |
| ⋮ | ⋮ |
| Twenty fifth storing part | |

BLOOD IMAGE ANALYZER

RELATED APPLICATIONS

This application claims priority from Japanese Patent Application 2006-324457 filed on Nov. 30, 2006, the disclosure of which is herein incorporated by reference in its entirety.

FIELD OF THE INVENTION

The present invention relates to blood image analyzers, in particular, to a blood image analyzer for analyzing a blood image obtained by capturing an image of a sample.

BACKGROUND

Conventionally, a blood image analyzer for analyzing a blood image obtained by capturing an image of a sample (see e.g., Japanese Laid-Open Patent Publication No. 11-83726).

In the blood image analyzer of Japanese Laid-Open Patent Publication No. 11-83726, a cassette accommodating a plurality of slide samples to be analyzed is set in the apparatus to analyze each slide sample. In such blood image analyzer, each slide sample accommodated in the cassette set in the apparatus is displayed in matrix form on a screen in frame format. The cell representing each slide sample is displayed by color in correspondence to the processing state ("non-processed", "no slide", "in counting", "in review", "processed", "count terminated", and "error") of each slide sample. The user then can understand the processing state of each slide sample from the screen.

However, at which position in the apparatus the slide sample in process is positioned cannot be recognized by simply looking at the screen in the blood image analyzer of Japanese Laid-Open Patent Publication No. 11-83726. Thus, when the apparatus stops due to error etc., it takes time to look for the slide sample in the apparatus, and it is difficult to perform rapid response on the slide sample in process in the apparatus.

Therefore, a blood image analyzer enabling the user to rapidly respond to the slide sample in process in the apparatus is desired.

SUMMARY

The scope of the present invention is defined solely by the appended claims, and is not affected to any degree by the statements within this summary.

A first blood image analyzer for analyzing a blood image embodying features of the present invention includes: an image capturing unit for capturing a blood image of a sample; an analyzing part for analyzing the sample based on the blood image captured by the image capturing unit; an identification information reader for reading, from the sample, identification information assigned to the sample; a transportation part for transporting the sample to the identification information reader and the image capturing unit; a first detector for detecting the sample at a first detection position on a pathway of the sample transported by the transportation part; a display; and a controller for controlling the display, so as to display, based on a detection result by the first detector, a screen including a first identification information display region, wherein the first identification information display region displays identification information of the sample being at the first detection position.

A second blood image analyzer for analyzing a blood image embodying features of the present invention includes: an image capturing unit for capturing a blood image of a sample; an analyzing part for analyzing the sample based on the blood image captured by the image capturing unit; a storing part setting unit for setting a storing part for storing the sample whose image has been captured by the image capturing unit, a first transportation part for transporting the sample to a relay position; a second transportation part for transporting the sample from the relay position to an image capturing region where image is captured by the image capturing unit, and transporting the sample from the image capturing region to the relay position; a third transportation part for transporting the sample whose image has been captured by the image capturing unit from the relay position to the storing part set in the storing part setting unit; first, second, and third sample detectors for detecting the sample at the first transportation part, the second transportation part, and the third transportation part; a display; and a controller for controlling the display, based on detection results of the first, second, and third sample detectors, so as to display a screen including sample position display region for displaying that the sample is positioned at one of a pathway of the first transportation part, a pathway of the second transportation part, or a pathway of the third transportation part.

A third blood image analyzer for analyzing a blood image embodying features of the present invention includes: an image capturing unit for capturing a blood image of the sample; an analyzing part for analyzing the blood image; a transportation part for transporting the sample along a pathway to/from the image capturing unit; detectors for detecting the location of the sample on the pathway; a display; and a controller for controlling the display, so as to display, based on detection results by the detectors, information regarding the location of the sample.

BRIEF DESCRIPTION OF THE DRAWINGS

FIG. 18 is a flowchart describing the processing operation of the slide glass of the automatic blood image analyzer shown in FIG. 1;

FIG. 19 is a conceptual view showing a storage table; and

FIG. 20 is a conceptual view showing the storage table after transportation.

DETAILED DESCRIPTION OF THE PREFERRED EMBODIMENTS

An embodiment embodying the present invention will now be described based on the drawings.

Figure 1:
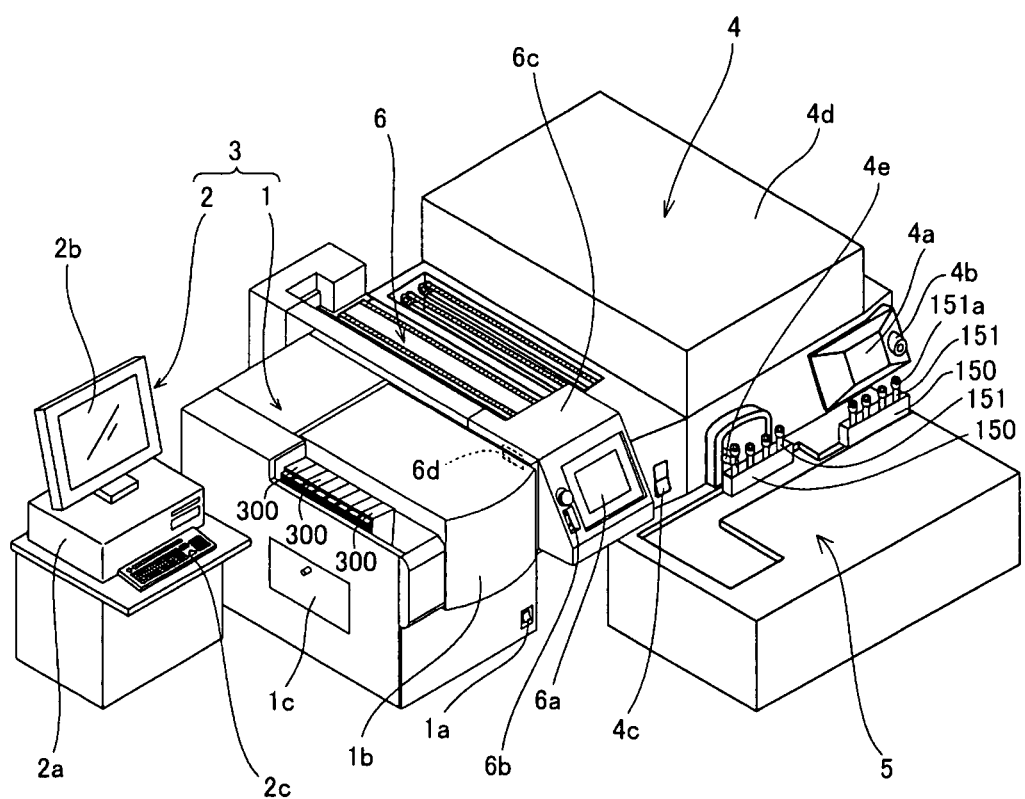
FIG. 1 is a perspective view showing an overall configuration of a sample image capturing system including an automatic blood image analyzer according to one embodiment of the present invention.

FIG. 1 is a perspective view showing an overall configuration of a sample image capturing system including a blood image analyzer according to one embodiment of the present invention. FIGS. 2 to 16 are views describing detailed configuration of the sample image capturing device of the blood image analyzer according to one embodiment shown in FIG. 1. First, the configuration of the blood image analyzer 3 according to one embodiment of the present invention will be described with reference to FIGS. 1 to 16.

The blood image analyzer 3 according to one embodiment of the present invention is configured by a sample image capturing device 1 and a control device 2. The blood image analyzer 3 is provided in the sample image capturing system for automatically preparing a blood sample, capturing the blood image, and analyzing the sample. As shown in FIG. 1, the sample image capturing system includes the blood image analyzer 3 configured by the sample image capturing device 1 and the control device 2; a blood smear sample preparing device 4; a specimen transporting device 5; and a sample transporting device 6. The sample image capturing system is a system of transporting the blood sample (slide glass) prepared for a specimen (blood) retrieved from the specimen transporting device 5 in the blood smear sample preparing device 4 to the sample image capturing device 1 by means of the sample transporting device 6, capturing the image of the transported blood sample (slide glass) in the sample image capturing device 1, and automatically performing categorization of blood cells through digital image processing of the captured image by the control device 2.

Figure 4:
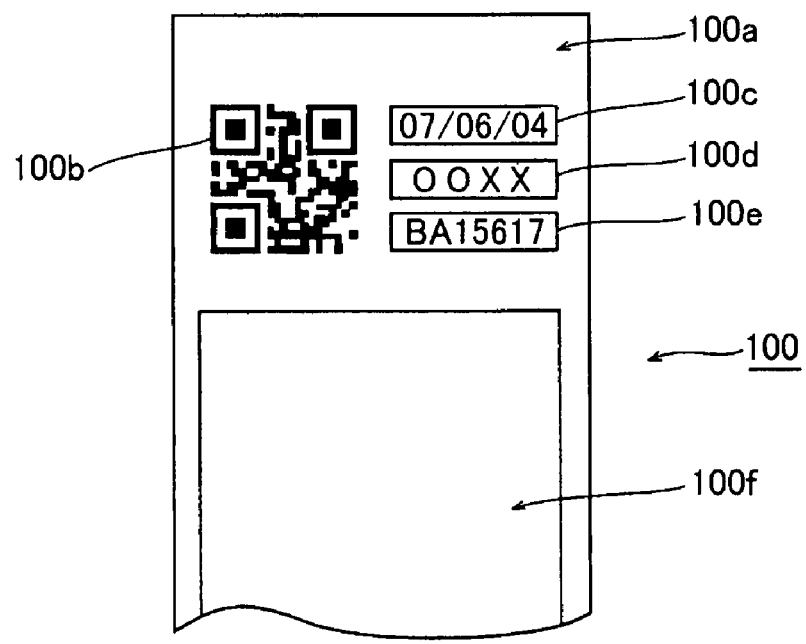
FIG. 4 is a plan view showing a slide glass used in the sample image capturing system shown in FIG. 1.

The blood smear sample preparing device 4 is a device for preparing an automatically analyzable sample that can be analyzed by the sample image capturing device 1 on a slide glass 100. The blood smear sample preparing device 4 has a processing ability of preparing 120 slide glasses 100 with sample per hour. As shown in FIG. 4, a two-dimensional barcode 100b stored with sample information such as specimen number (ID), date, reception number, name and the like; a date 100c (Jul. 6, 2004 in FIG. 4) serving as attribute information contained in the sample information; patient's name 100d (○○× × in FIG. 4); and one part 100e of the specimen number (ID) (BA15617 in FIG. 4) are printed in a frost part (information display region) 100a of the slide glass 100 prepared in the blood smear sample preparing device 4 by a thermal transfer printer (not shown) incorporated in the blood smear sample preparing device 4.

As shown in FIG. 1, the blood smear sample preparing device 4 includes a display operation unit 4a including a touch panel, an activation switch 4b, a power switch 4c, and a cover 4d. The blood smear sample preparing device 4 is also arranged with a hand member 4e for transporting a test tube 151 accommodating the blood from the specimen transporting device 5 side to the blood smear sample preparing device 4 side. A rubber plug 151a is attached to the test tube 151 accommodating the blood. As shown in FIG. 1, the specimen transporting device 5 is provided to automatically transport a specimen rack 150 for storing the test tube 151 accommodating the blood to the blood smear sample preparing device 4.

Figure 5:
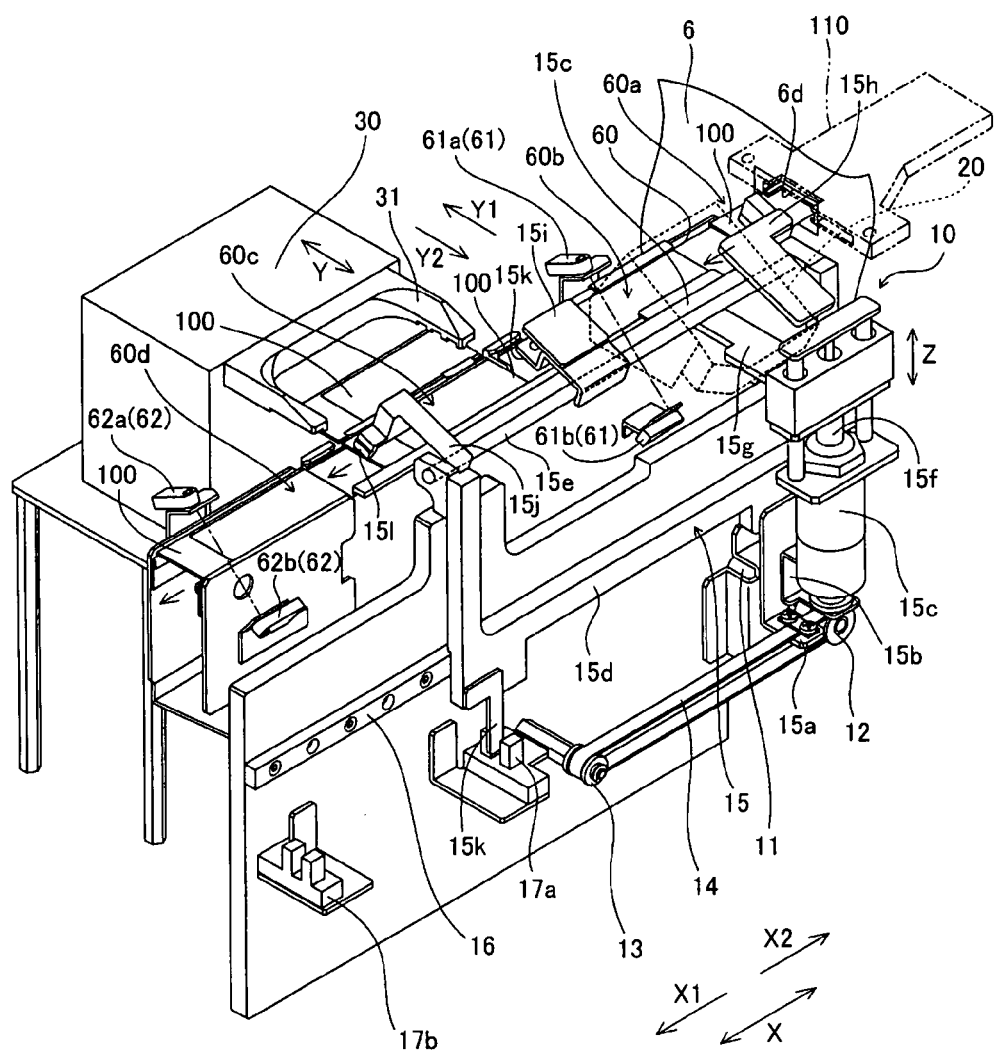
FIG. 5 is a perspective view describing the details of the sample image capturing device shown in FIG. 2.

As shown in FIG. 1, the sample transporting device 6 is provided to transport the slide glass 100 accommodated in the cassette 110 (see FIG. 5) received from the blood smear sample preparing device 4 to the sample image capturing device 1. As shown in FIG. 1, the sample transporting device 6 includes a display 6a, a power switch 6b, and a cover 6c. As shown in FIG. 5, the sample transporting device 6 is configured to transfer the slide glass 100 whose image is to be captured to the sample image capturing device 1 through a transfer port 6d.

In the present embodiment, the sample image capturing device 1 has a function of capturing an image of the sample formed in a sample preparation region 100f (see FIG. 4) of the slide glass 100 received from the sample transporting device 6. The sample image capturing device 1 has a processing ability of capturing 90 images per hour on the sample on the slide glass 100. As shown in FIG. 1, the sample image capturing device 1 includes a power switch 1a, an openable/closeable cover 1b, and a lid 1c arranged on the side surface of a housing in an openable/closeable manner. The control device 2 is electrically connected to the sample image capturing device 1.

Figure 2:
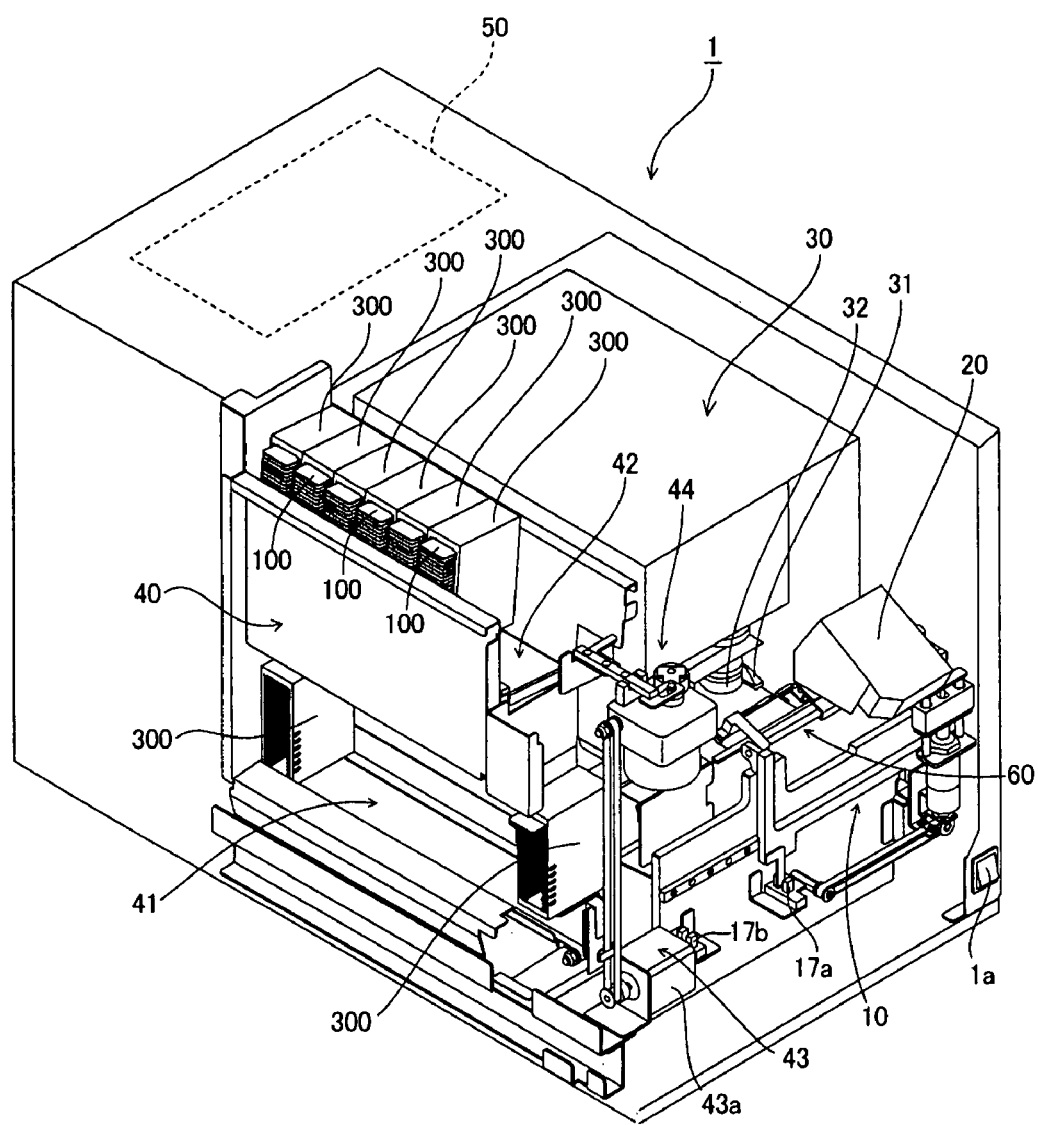
FIG. 2 is a perspective view showing the sample image capturing device of the automatic blood image analyzer shown in FIG. 1.
Figure 3:
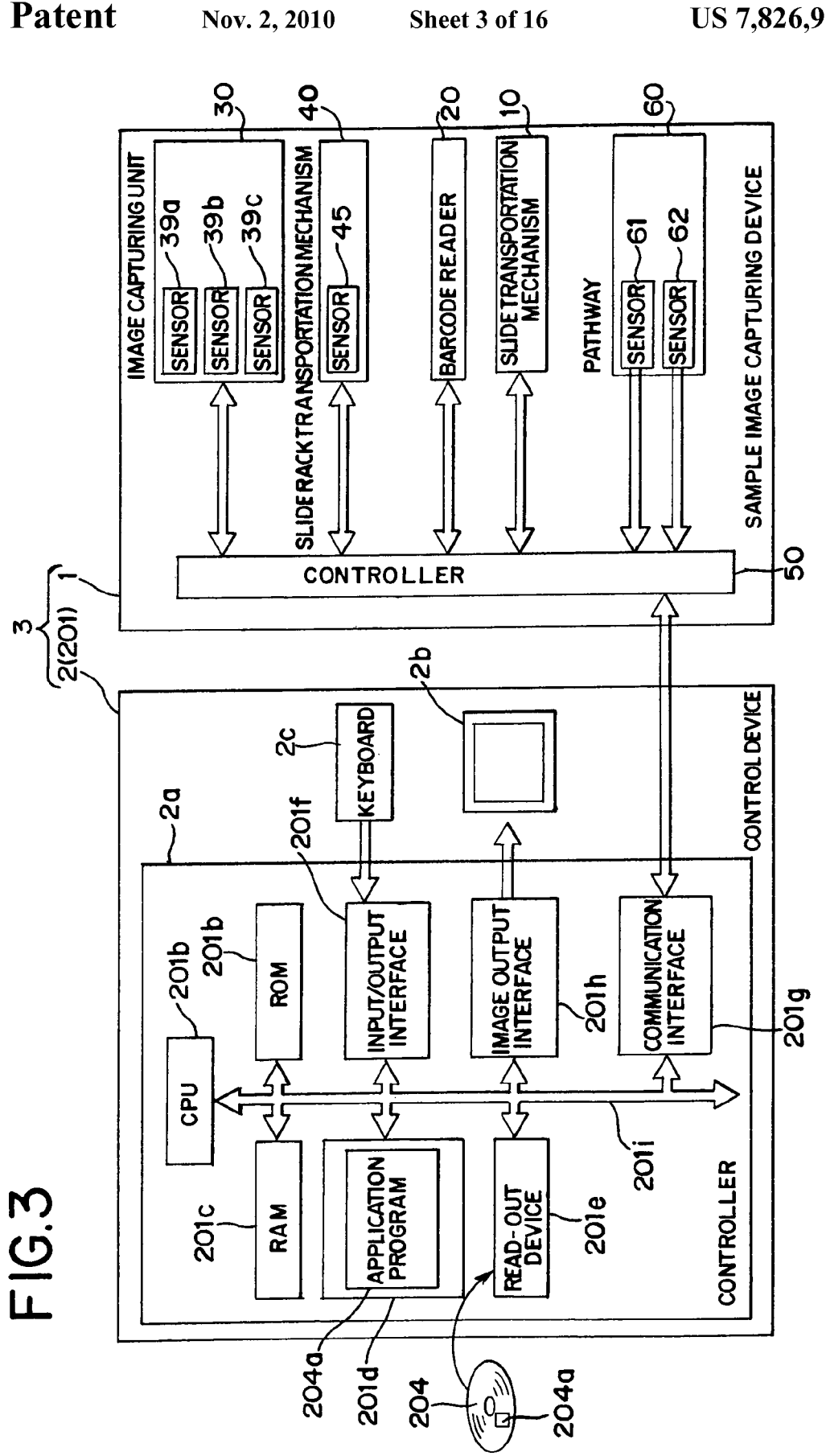
FIG. 3 is a block diagram showing the automatic blood image analyzer shown in FIG. 1.

As shown in FIGS. 2 and 3, the sample image capturing device 1 is configured by a slide transportation mechanism 10, a barcode reader 20, an image capturing unit 30, a slide rack transportation mechanism 40, and a controller 50. The slide glass 100 is configured so as to be transported along a pathway 60 in the sample image capturing device 1.

Figure 6:
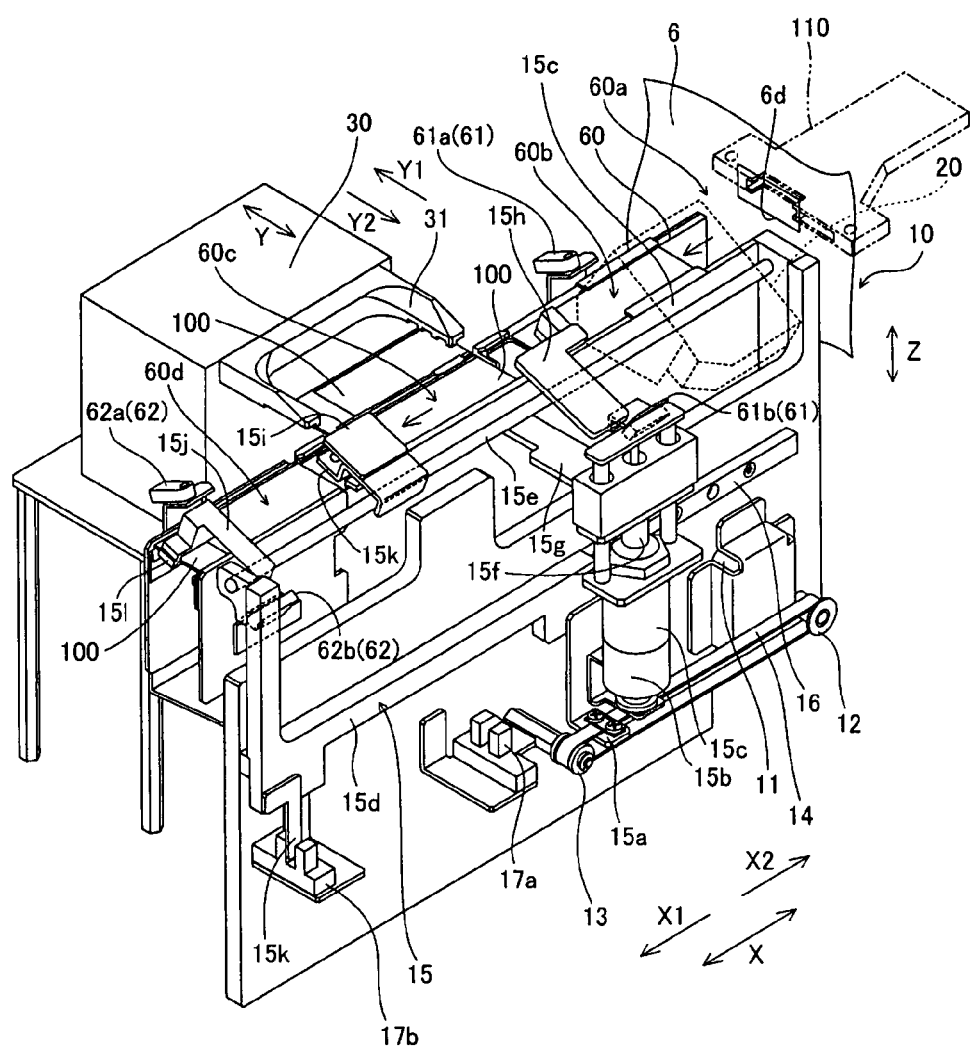
FIG. 6 is a perspective view describing the details of the sample image capturing device shown in FIG. 2.
Figure 7:
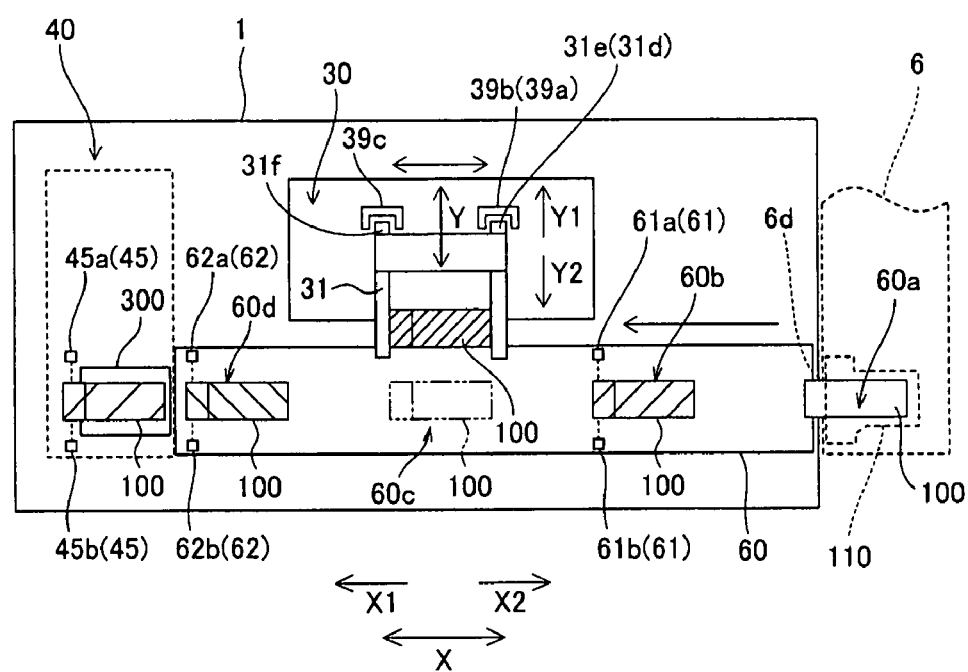
FIG. 7 is a plan view showing in frame format the sample image capturing device shown in FIG. 5.

As shown in FIGS. 5 to 7, the slide transportation mechanism 10 has a function of retrieving the slide glass 100 through the transfer port 6d of the sample transporting device 6 from the cassette 110 arranged horizontally in the sample transporting device 6, and transporting the retrieved slide glass 100 to the barcode reader 20. The slide transportation mechanism 10 also has a function of transporting the slide glass 100 in the X1 direction. The slide transportation mechanism 10 is configured by a stepping motor 11, a pulley 12 connected to the stepping motor 11, a pulley 13 arranged with a predetermined spacing from the pulley 12, a drive transmission belt 14 attached to the pulley 12 and the pulley 13, a movement mechanism 15 which moves with the drive transmission belt 14, a linear movement guide (slide rail) 16 for moving the movement mechanism 15 in the X direction, and two light shielding sensors 17a and 17b. Thus, the drive transmission belt 14 is driven by way of the pulley 12 when the stepping motor 11 is driven, and the movement mechanism 15 connected to the drive transmission belt 14 moves in the X direction.

Figure 8:
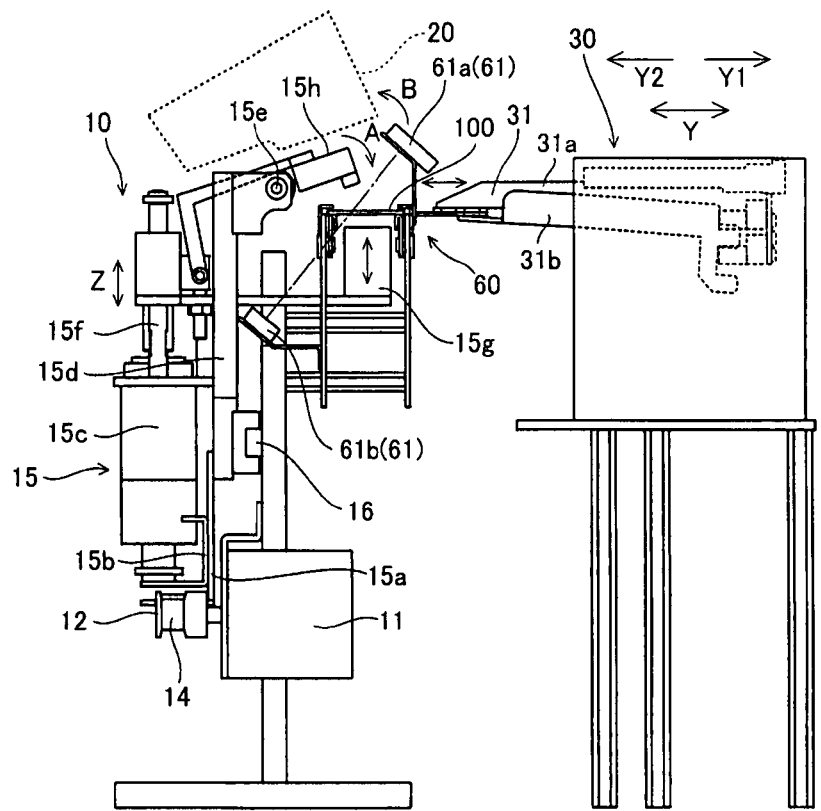
FIG. 8 is a side view of the sample image capturing device shown in FIG. 5.

As shown in FIGS. 5 and 8, the movement mechanism 15 is configured by a connecting member 15a connected to the drive transmission belt 14, a solenoid supporting member 15b attached to the connecting member 15a, a solenoid 15c supported by the solenoid supporting member 15b, a movement member 15d attached to the connecting member 15a and being movable along the linear movement guide (slide rail) 16, a supporting shaft 15e rotatably attached to the movement member 15d, a lower chuck part 15g which moves in the up and down direction (Z direction) with a rod 15f of the solenoid 15c, an upper chuck part 15h attached to the supporting shaft 15e and turned in a direction of the arrow A and in a direction of the arrow B (see FIG. 8) in cooperation with the lower chuck part 15g, and pressing parts 15i (see FIG. 5) and 15j (see FIG. 5) attached to the supporting shaft 15e. When the rod 15f of the solenoid 15c is extended in the Z direction, the lower chuck part 15g is moved in the Z direction to support the lower surface of the slide glass 100 in the pathway 60. In this case, the upper chuck part 15h is turned in the direction of the arrow A with the supporting shaft 15e in cooperation with the movement in the Z direction (upward direction) of the lower chuck part 15g to support the lower surface of the slide glass 100 in the pathway 60. Therefore, the slide glass 100 of the pathway 60 is gripped by the lower chuck part 15g and the upper chuck part 15h. Furthermore, since the pressing parts 15i and 15j are also attached to the supporting shaft 15e, the pressing parts 15i (see FIG. 5) and 15j (see FIG. 5) also turn in the direction of the arrow A and in the direction of the arrow B in cooperation with the turning of the upper chuck part 15h in the direction of the arrow A and in the direction of the arrow B. Moreover, a detection strip 15k for light shielding the two light shielding sensors 17a and 17b is arranged on the movement member 15d, and the position of the movement mechanism 15 is detected by the two light shielding sensors 17a and 17b, as shown in FIG. 5.

As shown in FIGS. 5 and 6, the upper chuck part 15h and the lower chuck part 15g have a function of gripping the slide glass 100 arranged at an introducing position 60a of the pathway 60, and transporting the slide glass 100 in the X1 direction up to a barcode reading position 60b of the barcode reader 20. The lower chuck part 15g has a function of transporting the slide glass 100 being at the barcode reading position 60b from the barcode reading position 60b to a drawing position 60c by contacting the end face on the X2 direction side of the slide glass 100 being at the barcode reading position 60b and pushing out the slide glass in the direction of the arrow X1 when the upper chuck part 15h and the lower chuck part 15g grip the slide glass 100 positioned at the introducing position 60a and move the slide glass 100 in the direction of the arrow X1. The pressing part 15i is configured to push out the slide glass 100 in the direction of the arrow X1 as a result of contact between the end face on the X2 direction side of the slide glass 100 positioned at the drawing position 60c and the contacting part 15k when the movement mechanism 15 moves in the direction of the arrow X1 while being turned in the direction of the arrow A (see FIG. 8). The slide glass 100 is transported from the drawing position 60c to a slide rack storage waiting position 60d by the pressing part 15i. The pressing part 15j is configured to push out the slide glass 100 in the direction of the arrow X1 as a result of contact between the end face on the X2 direction side of the slide glass 100 positioned at the slide rack storage waiting position 60d and the contacting part 15k when the movement mechanism 15 moves in the direction of the arrow X1 while being turned in the direction of the arrow A (see FIG. 8). The pressing part 15j stores the slide glass 100 from the slide rack storage waiting position 60d to a slide rack 300 (see FIGS. 12 and 13) set in the slide rack transportation mechanism 40.

Furthermore, the barcode reader 20 includes a two-dimensional barcode reader and has a function of reading the two-dimensional barcode 100b (see FIG. 4) printed in the frost part 100a of the slide glass 100. The control device 50 recognizes the ID of the slide glass 100 when the two-dimensional barcode 100b is read by the barcode reader 20. In the present embodiment, a transmissive sensor (hereinafter referred to as first sensor) 61 configured by a light emitting part 61a and a light receiving part 61b attached so that the barcode reading position 60b of the pathway 60 is in between is arranged. The slide glass 100 being at the barcode reading position 60b is detected by the sensor (first sensor) 61.

Figure 9:
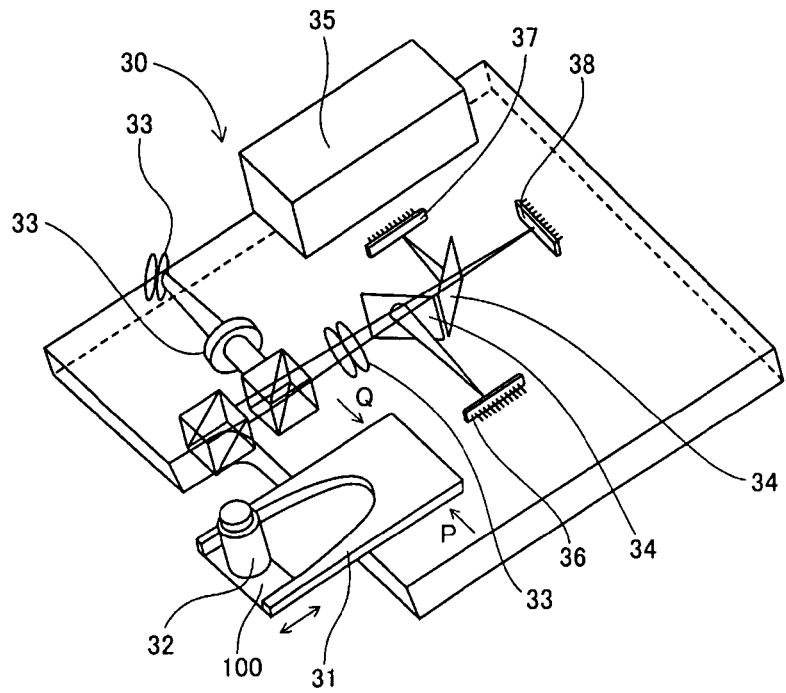
FIG. 9 is a perspective view showing in frame format an image capturing unit of the sample image capturing device shown in FIG. 5.

As shown in FIGS. 5, 7, and 9, the image capturing unit 30 is arranged to capture the sample image (not shown) formed in the sample preparation region 100f (see FIG. 4) of the slide glass 100. As shown in FIG. 9, the image capturing unit 30 includes a slide chuck 31 movable in the Y direction, an objective lens 32, a plurality of lenses 33, a half mirror 34, a CCD camera 35, line sensors 36 to 38, and three transmissive sensors 39a to 30c (see FIGS. 7, 10, and 11).

Figure 10:
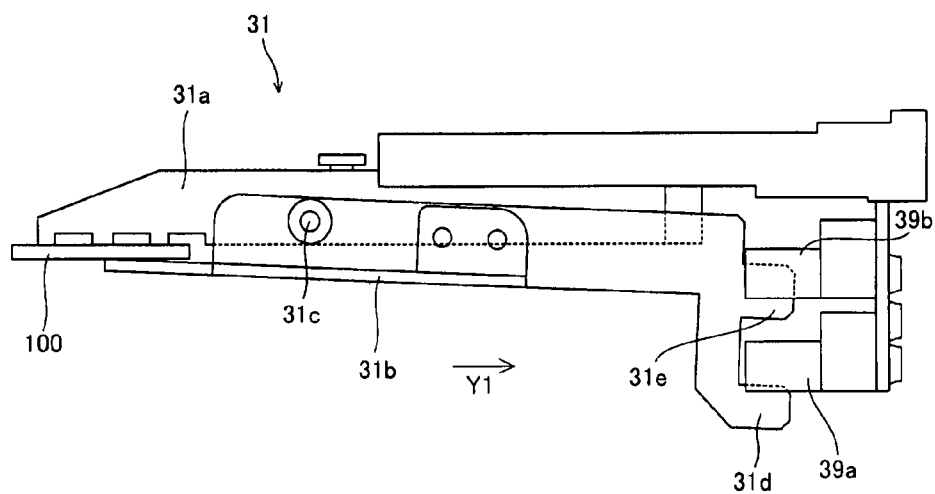
FIG. 10 is a side view showing a state seen from direction of an arrow P of the slide chuck of the image capturing unit shown in FIG. 9.
Figure 11:
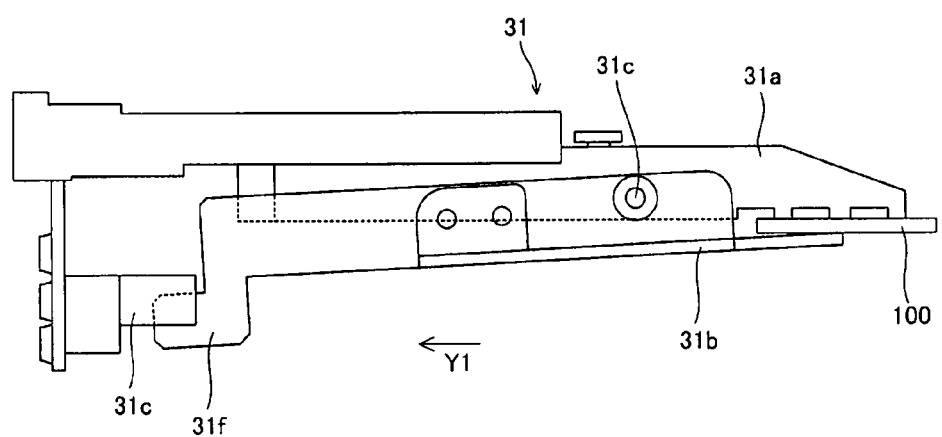
FIG. 11 is a side view showing a state seen from direction of an arrow Q of the slide chuck of the image capturing unit shown in FIG. 9.

Furthermore, the slide chuck 31 is configured by an upper chuck 31a and a lower chuck 31b, as shown in FIGS. 10 and 11. The lower chuck 31b can be turned with respect to the upper chuck 31a with a turning shaft 31c as the center. Two detection strips 31d and 31e projecting towards the back side (direction of arrow Y1) are arranged at the back end on the X2 direction side of the lower chuck 31b. One detection strip 31f projecting towards the back side (direction of arrow Y1) is arranged at the back end on the X1 direction side of the lower chuck 31b. The slide chuck 31 has a function of gripping the slide glass 100 transported to the drawing position 60c of the pathway 60 and thereafter moving the same towards the back side (direction of arrow Y1) to arrange the same at a position below the objective lens 32 when the lower chuck 31b is turned while being moved towards the front (direction of arrow Y2) side. As shown in FIGS. 7 and 10, sensors 39a and 30b are arranged at positions corresponding to the detection strips 31d and 31e. Furthermore, a sensor 39c is arranged at a position corresponding to the detection strip 31f as shown in FIGS. 7 and 11. A second sensor configured by the sensors 39a, 39b, and 39c is configured to detect the detection strips 31d, 31e, and 31f with the turning of the lower chuck 31b, so that the turning angle of the lower chuck 31b can be recognized by the controller 50.

Specifically, when the sensor 39a is in the ON state (state in which the sensor 39a detects the detection strip 31d), the lower chuck 31b is recognized by the controller 50 as being in the opened state regardless of whether the sensor 39b and the sensor 39c is turned ON/OFF. That is, the controller 50 recognizes that the slide glass 100 is not being chucked by the slide chuck 31. When the sensor 39a is in the OFF state (state in which the sensor 39a does not detect the detection strip 31d) and the sensor 39b and the sensor 39c are in the ON state, the controller 50 recognizes that the slide chuck 31 is in the closed state while gripping the slide glass 100. In other words, the controller 50 recognizes that the slide glass 100 is being chucked by the slide chuck 31 (slide glass 100 is positioned at the image capturing position). Moreover, when all of the sensors 39a to 39c are in the OFF state (state in which the sensors 39a to 39c do not detect the detection strips 31d to 31f), the controller 50 recognizes that the slide chuck 31 is in the closed state without gripping the slide glass 100. In other words, the controller 50 recognizes that the slide glass 100 is not being chucked by the slide chuck 31. The sensor configured by the sensors 39a, 39b, and 39c is turned ON when the slide glass 100 is positioned at the image capturing position (slide glass 100 is chucked by the slide chuck 31), and turned OFF when the slide glass 100 is not chucked by the slide chuck 31. The slide glass 100 being at the image capturing position is detected by the second sensor in such manner.

When the slide chuck 31 chucking the slide glass 100 is moved in the direction of the arrow Y2, the sample preparation region 100f of the slide glass 100 moves to below the objective lens 32. Then images of the sample of the sample preparation region 100f of the slide glass 100 arranged at the position below the objective lens 32 are captured by a CCD camera 35 through a plurality of lenses 33. The line sensor 36 has a function of detecting white blood cells specifically dyed blue. The line sensors 37 and 38 are used in focus adjustment of the CCD camera 35.

As shown in FIGS. 5 to 7, in the present embodiment, a transmissive sensor (hereinafter referred to as third sensor) 62 configured by a light emitting part 62a and a light receiving part 62b attached so as that the slide rack storage waiting position 60d of the pathway 60 is in between is arranged at the end on the X1 direction side of the pathway 60. The slide glass 100 being at the slide rack storage waiting position 60d is detected by the sensor (third sensor) 62.

Figure 12:
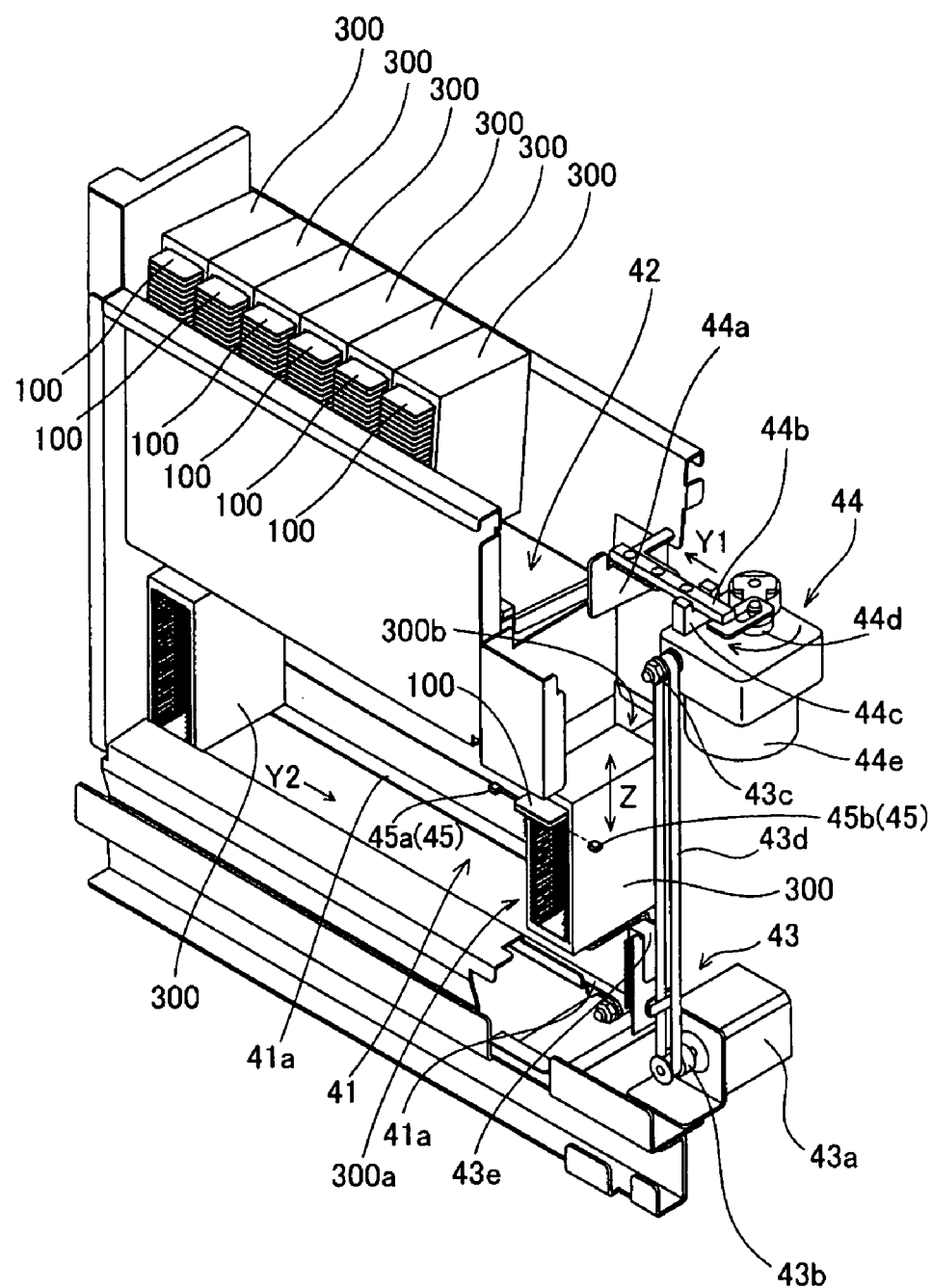
FIG. 12 is a perspective view showing a slide rack transportation mechanism of the sample image capturing device shown in FIG. 2.

As shown in FIG. 12, the slide rack transportation mechanism 40 is configured by slide rack storing units 41 and 42, a slide rack transferring unit 43, and a slide rack feeding unit 44. The slide rack transportation mechanism 40 has a function of transporting an empty slide rack 300 to be replenished to the slide rack storing unit 41 by opening the lid 4c (see FIG. 1) arranged in an openable/closeable manner on the side surface of the housing from the pathway 60 to a slide receiving position where the slide glass 100 is received, and transporting the slide rack 300 that has received the slide glass 100 from the slide receiving position to the slide rack storing unit 42.

As shown in FIG. 12, the slide rack storing unit 41 is arranged to store a plurality of empty slide racks 300. The slide rack storing unit 41 includes a pair of transportation belts 41a for transporting the slide rack 300 in the Y2 direction. The slide rack storing unit 42 is provided to store a plurality of slide racks 300 accommodating the slide glass 100. The slide rack storing units 41 and 42 respectively accommodates a maximum of eight slide racks 300.

Figure 13:
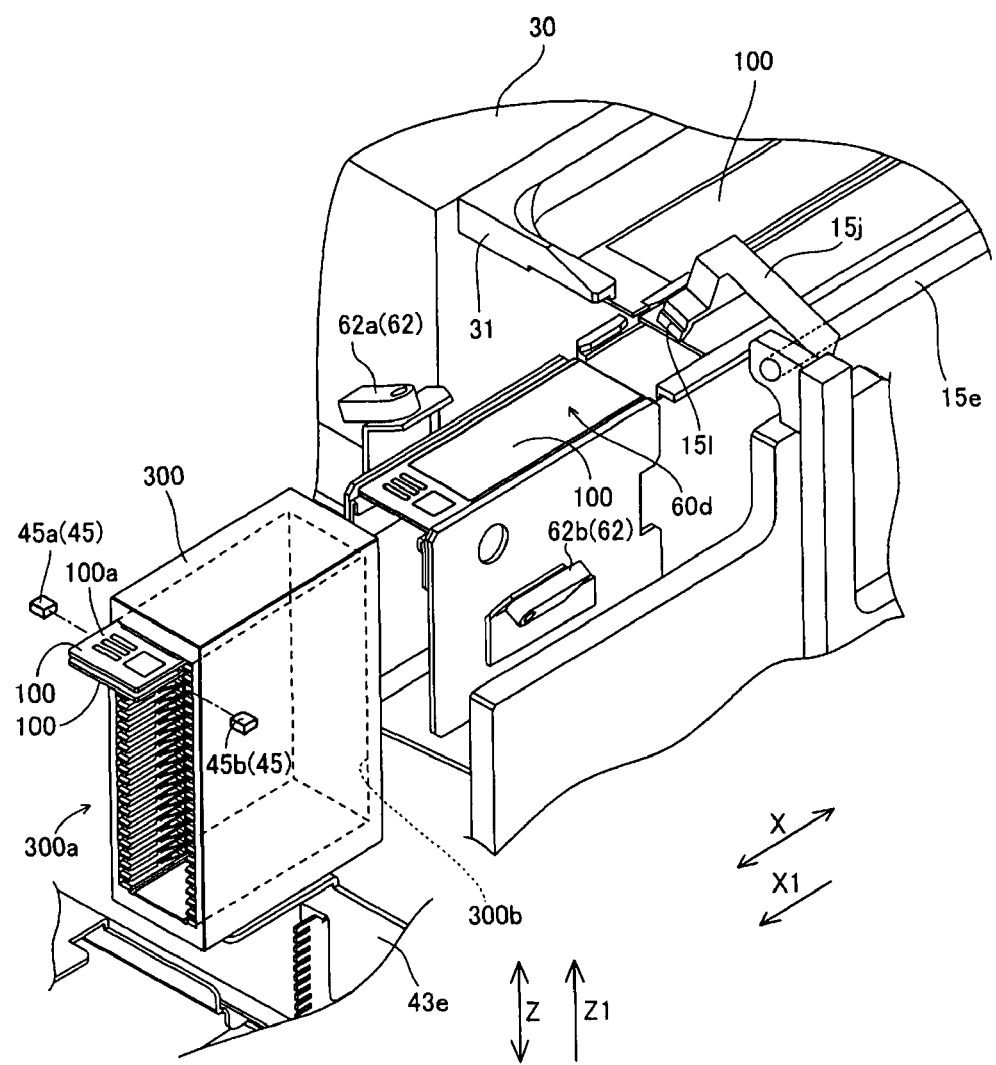
FIG. 13 is an enlarged perspective view of the slide rack transportation mechanism shown in FIG. 12.

The slide rack transferring unit 43 is configured to transfer the empty slide rack 300 from the slide rack storing unit 41 on the lower side to the slide rack storing unit 42 on the upper side through the slide receiving position. As shown in FIG. 12, the slide rack transferring unit 43 includes a stepping motor 43a, a pulley 43b connected to the shaft of the stepping motor 43a, a pulley 43c arranged on the upper side with a predetermined spacing from the pulley 43b, a drive transmission belt 43d attached to the pulley 43b and the pulley 43c, and a transportation member 43e connected to the drive transmission belt 43d. When the stepping motor 43a is driven, the drive transmission belt 43d is driven by way of the pulley 43b, and the transportation member 43e connected to the drive transmission belt 43d moves in the Z direction. The transportation member 43e capable of mounting the slide rack 300 then can be moved to the upper side (direction of arrow Z1). As shown in FIG. 13, the slide glass 100 being at the slide rack storage waiting position 60d of the pathway 60 is pressed in the direction of the arrow X1 by the pressing part 15j of the slide transportation mechanism 10 with the empty slide rack 300 mounted on the transportation member 43e transported upward to the slide receiving position, so that the slide glass 100 is inserted into the slide rack 300.

Figure 14:
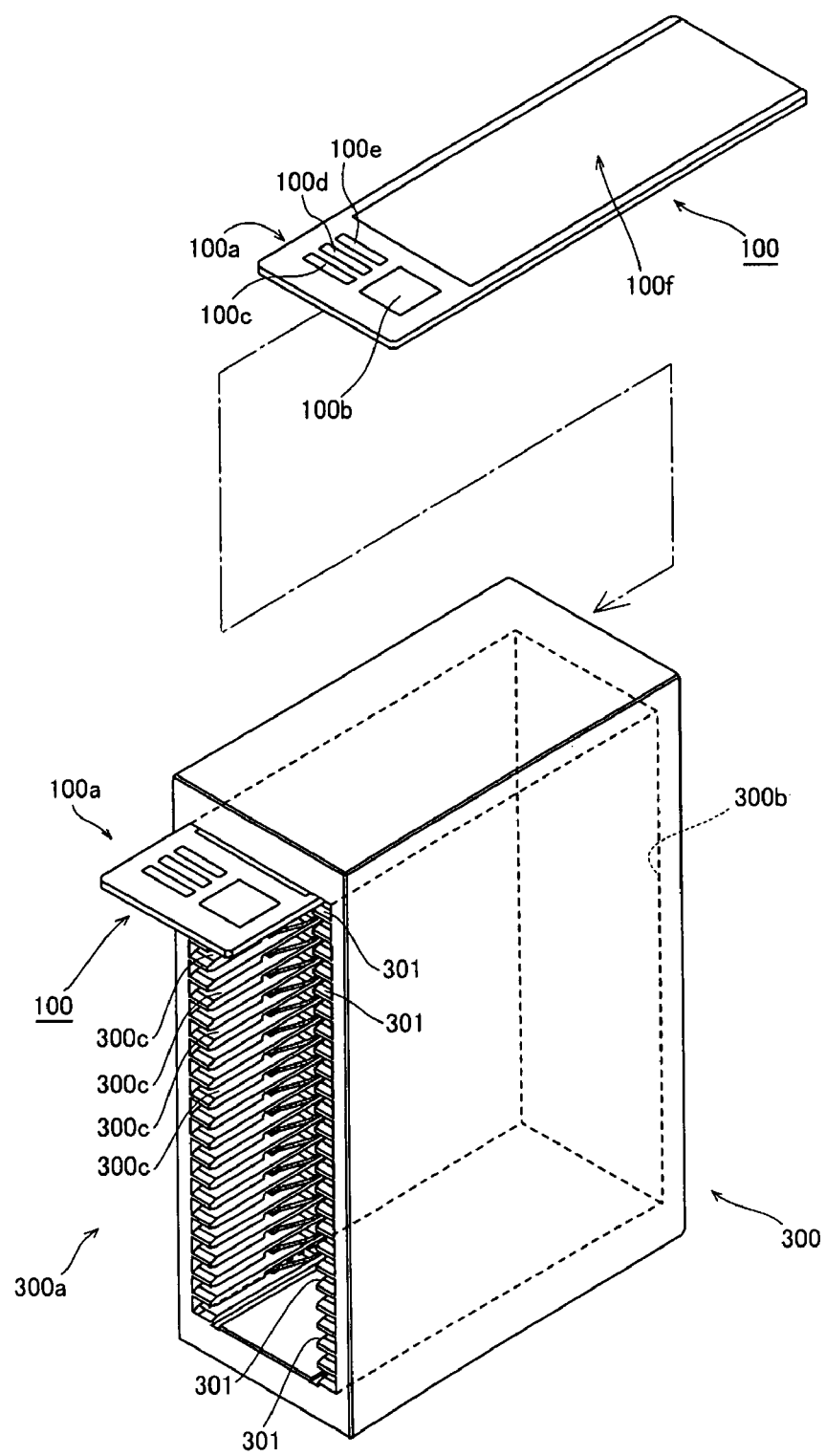
FIG. 14 is a perspective view showing a slide rack and a slide glass shown in FIG. 13.

As shown in FIG. 14, the slide rack 300 is formed into a hollow vertically long box shape and is formed with two openings 300a and 300b to enable the slide glass 100 to pass through in the transporting direction. A pair of shelf parts 301 projected towards the inner side and formed to extend from the opening 300a to the opening 300b is arranged on a pair of inner side surfaces. The pair of shelf parts 301 is arranged to support the vicinity of the side end of the slide glass 100. 25 pairs of shelf parts 301 are arranged in the up and down direction with a predetermined spacing, where each of the 25 shelf parts 301 function as a storing part 300c for storing one slide glass 100. In the present embodiment, the slide rack 300 being at the slide receiving position is transported upward by a predetermined distance (one storing unit 300c) by the slide rack transferring unit 43, and the slide glass 100 is sequentially inserted and stored in the storing part 300c positioned at the same height as the pathway 60. That is, the slide glass 100 is configured to be stored in order from the top in the 25 storing parts 300c of the slide rack 300. The slide glass 100 inserted to the storing part 300c from the pathway 60 through the opening 300b is stored in the storing part 300c with the portion including the frost part 100a projecting outward.

As shown in FIG. 13, in the present embodiment, a transmissive sensor (hereinafter referred to as fourth sensor) 45 configured by a light emitting part 45a and a light receiving part 45b is arranged at a position the same height as the pathway 60 and so that the frost part 100a of the slide glass 100 stored in the storing part 300c is in between. When the slide glass 100 is stored in the storing part 300c, the sensor (fourth sensor) 45 detects the frost part 100a projecting out from the storing part 300c, so that the controller 50 detects that the slide glass 100 has been stored in the storing part 300c.

Furthermore, the slide rack feeding unit 44 has a function of feeding the slide rack 300 accommodating the slide glass 100 transferred to the upper side by the slide rack transferring unit 43 towards the slide rack storing unit 42 side, as shown in FIG. 12. The slide rack feeding unit 44 is configured by a push-out member 44a, a movable slide rail 44b, a slide rail supporting member 44c for movably supporting the slide rail 44b, an arm 44d and a motor 44e. The push-out member 44a is attached to the slide rail 44b. and the slide rail 44b is arranged so as to extend in the Y direction. One end of the arm 44d is attached to the slide rail 44b through a long hole, and the other end is connected to a rotation shaft of the motor 44e. Accordingly, when the motor 44e is driven, one end of the arm 44d is turned, so that the slide rail 44b moves in the Y1 direction with respect to the slide rail supporting member 44c. Therefore, the push-out member 44a moves along the Y1 direction. The slide rack 300 transferred to the upper side by the slide rack transferring unit 43 is then pressed against the push-out member 44a and pushed out towards the slide rack storing unit 42 side.

As shown in FIG. 3, the controller 50 has a function of controlling the operation of the slide transportation mechanism 10, the barcode reader 20, the image capturing unit 30, and the slide rack transportation mechanism 40. The controller 50 also has a function of acquiring digital data of the sample image captured by the image capturing unit 30, and sequentially transmitting the data to a controller 2a of the control device 2. The controller 50 furthermore has a function of acquiring information (slide ID etc.) of the barcode read by the barcode reader 20, and transmitting the information to the controller 2a of the control device 2. In the present embodiment, the controller 50 monitors whether transportation of the slide glass 100 is being properly performed by receiving signals from the second sensor including the sensors 39a to 39c of the image capturing unit 30, the sensors (first sensor) 61 and (third sensor) 62 of the pathway 60, and the sensor (fourth sensor) 45 of the slide rack transportation mechanism 40.

The control device 2 has a function of digital image processing the image of the sample on the slide glass captured by the image capturing unit 30 of the sample image capturing device 1 and automatically performing categorization of blood cells. As shown in FIG. 3, the control device 2 is made up of a personal computer (PC) 201, and the like, and includes the controller 2a, a display 2b and a keyboard 2c. The controller 2a is made up of CPU, ROM, RAM, and the like. The controller 2a has a function of instructing the controller 50 of the sample image capturing device 1 to perform the process of each mechanism (slide transportation mechanism 10 etc.) of the sample image capturing device 1. The controller 2a has a function of receiving from the controller 50 the digital data of the captured image acquired by the controller 50 from the image capturing unit 30, and analyzing the sample image (see FIG. 15) captured by the image capturing unit 30 based on the received data.

The configuration of the control device 2 will now be described. As shown in FIG. 3, the controller 2a is mainly configured by a CPU 201a, a ROM 201b, a RAM 201c, a hard disc 201d, a read-out device 201e, an input/output interface 201f, a communication interface 201g, and an image output interface 201h. The CPU 201a, the ROM 201b, the RAM 201c, the hard disc 201d, the read-out device 201e, the input/output interface 201f, the communication interface 201g, and the image output interface 201h are connected by a bus 201i.

The CPU 201a executes computer programs stored in the ROM 201b and the computer programs loaded in the RAM 201c. The computer 201 serves as the control device 2 when the CPU 201a executes the application program 204a, as hereinafter described.

The ROM 201b is configured by mask ROM, PROM, EPROM, EEPROM, and the like, and is recorded with computer programs to be executed by the CPU 201a, data used for the same, and the like.

The RAM 201c is configured by SRAM, DRAM, and the like. The RAM 201c is used to read out the computer programs recorded on the ROM 201b and the hard disc 201d. The RAM 201c is used as a work region of the CPU 201a when executing the computer programs. The content (ID etc.) of the two-dimensional barcode 100b of the slide glass 100 acquired by the barcode reader 20 and the sample image captured by the image capturing unit 30 are stored in the RAM 201c in correspondence to each other. The content (ID etc.) of the two-dimensional barcode 100b of the slide glass 100 acquired by the barcode reader 20 and the position (position of storing part 300c) of the sample (slide glass 100) stored in the slide glass 300 are stored in the RAM 201c in correspondence to each other.

The hard disc 201d is installed with various computer programs to be executed by the CPU 201a such as operating system and application program, as well as data used in executing the computer program. The application program 204a for categorizing the blood cells according to the present embodiment is also installed in the hard disc 201d.

The read-out device 201e is configured by flexible disc drive, CD-ROM drive, DVD-ROM drive, and the like, and is able to read out computer programs and data recorded on a portable recording medium 204. The application program 204a according to the present embodiment is stored in the portable recording medium 204, where the computer 201 reads out the application program 204a from the portable recording medium 204, and installs the application program 204a to the hard disc 201d.

The application program 204a is not only provided by the portable recording medium 204, but also provided through communication line (wired or wireless) from external devices communicatably connected with the computer 201 through the communication line. For instance, the application program 204a may be stored in the hard disc of the server computer on the Internet, so that the computer 201 can access the server computer to download the application program 204a and install the application program 204a to the hard disc 201d.

Operating system providing graphical user interface environment such as Windows (registered trademark) manufactured and sold by US Microsoft Co. is installed in the hard disc 201d. In the following description, the application program 204a according to the present embodiment is assumed to operate on the operating system.

The input/output interface 201f is configured by serial interface such as USB, IEEE1394, RS-232C; parallel interface such as SCSI, IDE, IEEE1284; analog interface such as D/A converter, A/D converter, and the like. The keyboard 2c is connected to the input/output interface 201f, so that the user can input data to the computer 201 using the keyboard 2c.

The communication interface 201g is, for example, Ethernet (registered trademark) interface. The computer 201 transmits and receives data with the controller 50 using a predetermined communication protocol by means of the communication interface 201g.

The image output interface 201h is connected to the display 2b configured by LCD, CRT, or the like, and is configured to output an image signal corresponding to the image data provided from the CPU 201a to the display 2b. The display 2b displays the image (screen) according to the input image signal.

Figure 15:
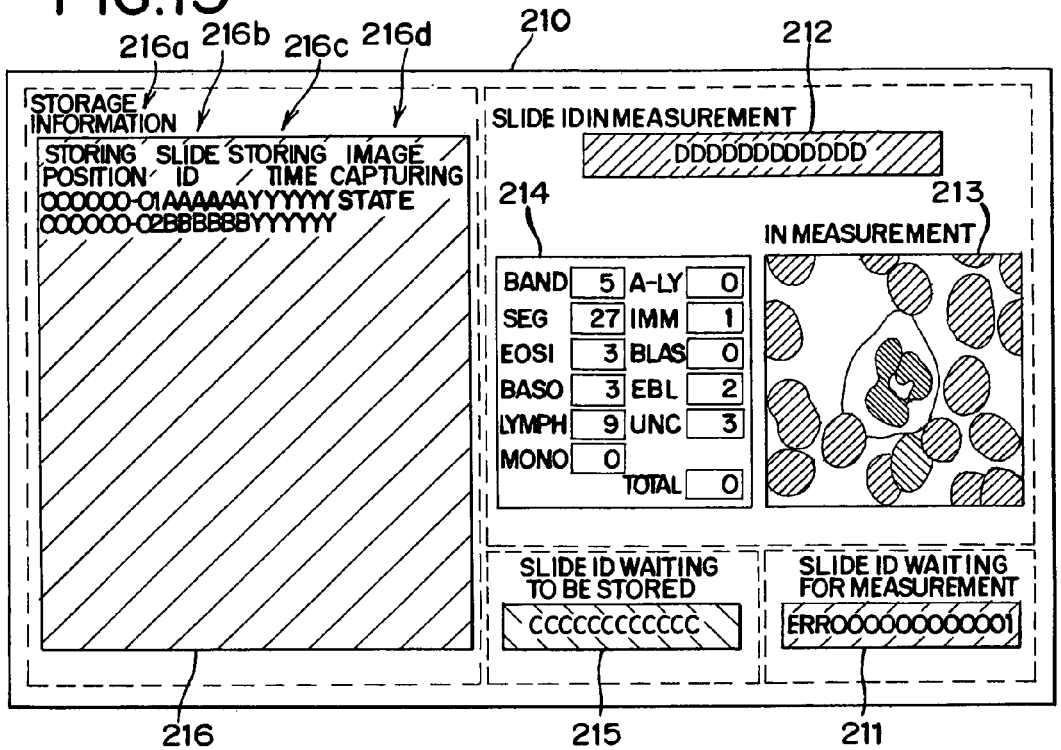
FIG. 15 is a view showing an analyzing state screen for displaying the processing state of the slide glass of the sample image capturing device displayed on the display of the control device.
Figure 16:
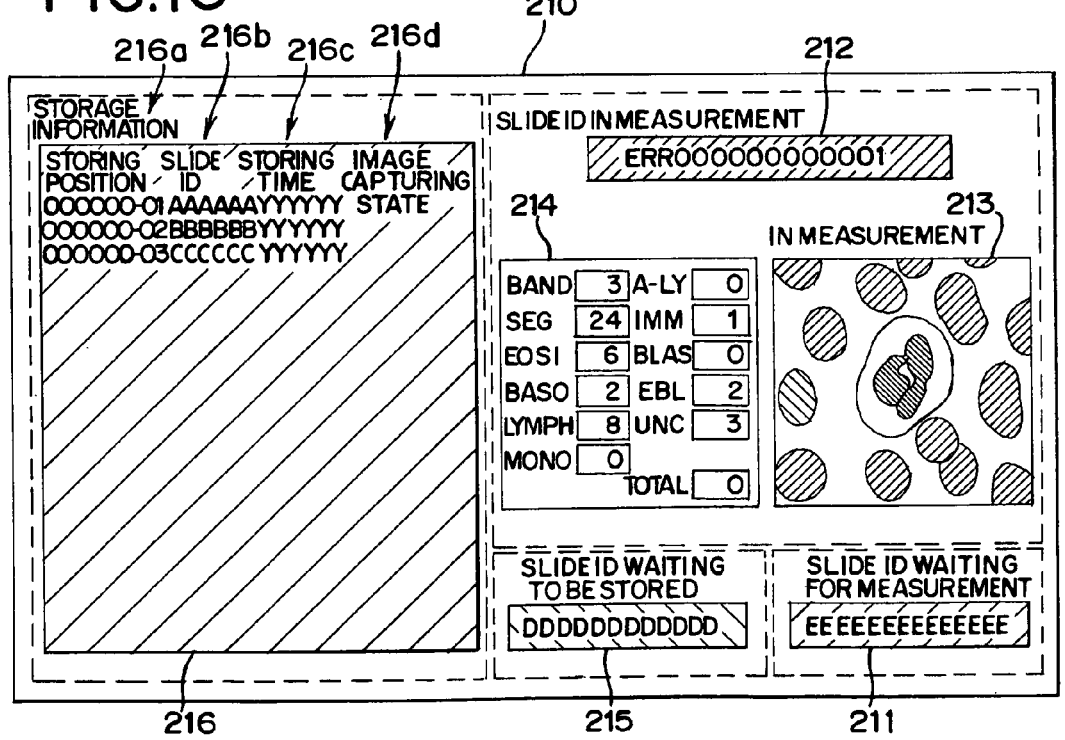
FIG. 16 is a view showing an analyzing state screen for displaying the processing state of the slide glass of the sample image capturing device displayed on the display of the control device.

As shown in FIGS. 15 and 16, the control device 2 is configured to display an analyzing state screen 210 for displaying the analyzing state on the display 2b during analysis in the present embodiment. The analyzing state screen 210 includes a first ID display region 211 for displaying the ID of the slide glass 100 being at the barcode reading position 60b, a second ID display region 212 for displaying the ID of the slide glass 100 (chucked by the slide chuck 31) being at the image capturing position, an image display region 213 for displaying the image captured by the image capturing unit 30, an analysis result display region 214 for displaying the result of analysis, a third ID display region 215 for displaying the ID of the slide glass 100 being at the slide rack storage waiting position 60d, and a fourth ID display region 216 for displaying the ID of the slide glass 100 stored in the slide rack 300.

As shown in FIGS. 7 and 15, the positional relationship of the arrangement in the analyzing state screen 210 of the first ID display region 211, the second ID display region 212, the third ID display region 215, and the fourth ID display region 216 corresponds to the planar positional relationship of the arrangement of the barcode reading position 60b in the sample image capturing device 1, the image capturing unit 30 including the image capturing position, the slide rack storage waiting position 60d, and the slide rack 300.

Specifically, in FIG. 7 (plan view of the sample image capturing device 1), the image capturing unit 30 includes the slide chuck 31 for gripping the slide 100 when capturing the image of the sample. The barcode reading position 60b is arranged at the lower right of the image capturing unit 30, and the slide rack storage waiting position 60d is arranged at the lower left of the image capturing unit 30. Furthermore, the slide rack transportation mechanism 40 including the slide rack 300 is arranged on the left of the image capturing unit 30, the barcode reading position 60b, and the slide rack storage waiting position 60d. In FIG. 15, the first ID display region 211 is arranged at the lower right seen from the second ID display region 212, and the third ID display region 215 is arranged at the lower left seen from the second ID display region 212. The fourth ID display region 216 is arranged at the left of the second ID display region 212, the first ID display region 211, and the third ID display region 215.

Furthermore, the captured image of the sample (slide glass 100) in image capturing is sequentially displayed on the image display region 213. The result of analysis obtained by performing an analysis based on the captured image is displayed on the analysis result display region 214.

The fourth ID display region 216 includes a storing position display region 216a in which the numbers indicating each of the 25 storing parts 300c of the slide rack 300 are displayed, an ID display region 216b in which the ID of the slide glass 100 stored in the slide rack 300 is displayed, a storing time display region 216c in which the time the slide glass 100 is stored in the slide rack 300 is displayed, and an image capturing state display region 216b in which the image capturing state of the slide glass 100 is displayed.

25 storing part numbers are displayed in the storing position display region 216a in correspondence to the vertical position of the arrangement of the 25 storing parts 300c in the slide rack 300. Specifically, the storing part number (000000-01 in FIG. 15) corresponding to the storing part 300c positioned at the top of the slide rack 300 (first storing part) is displayed on the top level in the storing position display region 216a. The storing part number (000000-02 in FIG. 15) corresponding to the storing part 300c positioned second from the top of the slide rack 300 (second storing part) is displayed on the second level from the top in the storing position display region 216a.

The ID of the slide glass 100 stored in the storing part 300c corresponding to the storing part number displayed in the storing position display region 216a is displayed in the ID display region 216b. An error is displayed at the level corresponding to the ID of the slide glass 100 in the image capturing state display region 216d when the blood smear sample prepared on the slide glass 100 is incomplete and image capturing is not adequately performed.

The operation of the sample image capturing system according to the present embodiment will now be described with reference to FIGS. 1, 2, 4 to 6, 8, 9, 12, and 13.

First, the specimen rack 150 storing the test tube 151 accommodating the blood specimen is set in the specimen transporting device 5 with the activation switch 102 pressed to activate the blood smear sample preparing device 4 as shown in FIG. 1, as a suction and dispensing operation by the blood smear sample preparing device 4. The start switch for automatic suction displayed on the display operation part 1a is then pressed. The specimen rack 150 is then transported to the position where it can be gripped by the hand member 1e of the blood smear sample preparing device 4, and the test tube 151 accommodating the blood of the specimen rack 150 is transported to the blood smear sample preparing device 4 by the hand member 1e. The smear sample (slide glass 100) of the blood obtained from the test tube 151 is prepared in the blood smear sample preparing device 4.

The two-dimensional barcode 100b in which the sample information such as specimen number (ID), date, reception number, and name are stored in the frost part 100a of the slide glass 100, the date 100c, and the patient's name 100d, as shown in FIG. 4, are printed on the frost part 100a of the smear sample (slide glass 100) prepared in the blood smear sample preparing device 4. Thereafter, the slide glass 100 is stored in the cassette 100 and moved to the sample transporting device 6.

The cassette 110 storing the slide glass 100 is transported to the predetermined position by the sample transporting device 6, and arranged so that the slide glass 100 projects out from the transfer port 6d (see FIGS. 1 and 5). Subsequently, as shown in FIG. 5, the slide glass 100 is sent to the introducing position 60a where it can be gripped by the upper chuck part 15h and the lower chuck part 15g of the slide transportation mechanism 10 of the sample image capturing device 1.

The slide glass 100 sent to the introducing position 60a where it can be gripped by the upper chuck part 15h and the lower chuck part 15g of the slide transportation mechanism 10 of the sample image capturing device 1 is taken out from the cassette 110 in the slide transportation mechanism 10, and the slide glass 100 is transported to the reading position 60b by the barcode reader 20, as shown in FIGS. 5 and 6. Specifically, as shown in FIG. 8, the rod 15f of the solenoid 15c is extended in the Z direction, so that the lower chuck part 15g moves in the Z direction, and the lower surface of the slide glass 100 of the pathway 60 is supported. In this case, the upper chuck part 15h turns in the direction of the arrow A (see FIG. 8) with the supporting shaft 15e in cooperation with the movement in the Z direction (upward direction) of the lower chuck part 15g, and the lower surface of the slide glass 100 of the pathway 60 is supported. The slide glass 100 positioned at the introducing position 60a is thereby gripped by the lower chuck part 15g and the upper chuck part 15h. When the stepping motor 11 is driven by a predetermined pulse with the slide glass 100 gripped, the pulley 12 and the drive transmission belt 14 are driven, and the movement mechanism 15 connected to the drive transmission belt 14 is moved in the X1 direction by a predetermined distance, as shown in FIG. 6. As a result, the slide glass 100 gripped by the upper chuck part 15h and the lower chuck part 15 g is transported to the reading position 60b. Thereafter, the upper chuck part 15h is turned in the direction of the arrow B (see FIG. 8), and the movement mechanism 15 is moved in the direction of the arrow X2 with the lower chuck part 15g moved to the lower side, thereby returning to the position shown in FIG. 5.

As shown in FIG. 5, the two-dimensional barcode 100b printed on the frost part 100a of the slide glass 100 is read by the barcode reader 20 from the slide glass 100 transported to the reading position 60b of the barcode reader 20. The specimen number (ID) of the slide glass 100 read by the barcode reader 20 is then stored in the controller 50.

Subsequently, the slide glass 100 read by the barcode reader 20 contacts the lower chuck part 15g when the movement mechanism 15 is moved by a predetermined distance in the direction of the arrow X1 with the lower chuck part 15g moved to the upper side, and is pushed out in the direction of the arrow X1, as shown in FIG. 6. The slide glass 100 pushed out by the lower chuck part 15g is transported to the drawing position 60c where it can be gripped by the slide chuck 31. The movement mechanism 15 is then moved in the direction of the arrow X2, and returned to the state shown in FIG. 5.

As shown in FIG. 5, the slide glass 100 arranged at the drawing position 60c is gripped by the slide chuck 31 moved towards the front side (direction of arrow Y2) in synchronization with the movement of the slide glass 10 to the drawing position 60c, and drawn into the image capturing unit 30 when the slide chuck 31 is moved towards the back side (direction of arrow Y1). As a result, the slide glass 100 is arranged at a position below the objective lens 32, as shown in FIG. 9. Images of the sample on the slide glass 100 gripped by the slide chuck 31 are captured by the CCD camera 35 of the image capturing unit 30 through the plurality of lenses 33 and the half mirror 34. A plurality of sample images of the slide glass 100 (see FIG. 15) is then acquired. Thereafter, the sample image that has been captured by the CCD camera 35 of the image capturing unit 30 is sequentially sent to the controller 2a of the control device 2 through the controller 50.

The sample image (see FIG. 15) sent to the controller 2a of the control device 2 is image processed in the controller 2a, and categorization of blood cells is automatically performed.

The slide glass 100 whose images have been captured is then moved towards the front side (direction of arrow Y2) by the slide chuck 31 and returned to the drawing position 60c. The slide glass 100 returned to the drawing position 60c contacts the contacting part 15k and is pushed out in the direction of the arrow X1, as shown in FIG. 6, when the movement mechanism 15 is moved by a predetermined distance in the direction of the arrow X1 with the pressing part 15i turned in the direction of the arrow A (see FIG. 8). The slide glass 100 is then transported from the drawing position 60c to the slide rack storage waiting position 60d. The slide glass 100 waits, at the slide rack storage waiting position 60d, to be stored in the storing part 300c of the slide rack 300. The movement mechanism 15 is then moved in the direction of the arrow X2 with the pressing part 15i turned in the direction of the arrow B (see FIG. 8), and returned to the state shown in FIG. 5.

In this case, an empty slide rack 300 is transported to the upper side from the slide rack storing unit 41 of the slide rack transportation mechanism 40, and the storing part 300c (storing part 300c third from the top in FIG. 13) of the slide rack 300 is arranged at the same height (slide receiving position) as the pathway 60, as shown in FIGS. 12 and 13. At this state, the movement mechanism 15 is moved by a predetermined distance in the direction of the arrow X1 with the pressing part 15j turned in the direction of the arrow A (see FIG. 8), so that the slide glass 100 being at the slide rack storage waiting position 60d contacts the contacting part 15l and is pushed out in the direction of the arrow X1. As a result, the slide glass 100 positioned at the slide rack storage waiting position 60d is stored in the storing part 300c of the slide rack 300 through the opening 300b. After the slide glass 100 is stored in the storing part 300c, the slide rack 300 is moved upward by one level of the storing part 300c. The slide rack 300 then is able to store a new slide glass 100. The slide glass 100 is sequentially stored in order from the top to the 25 storing parts 300c of the slide rack 300 in such manner.

The analysis of the sample image capturing system is performed in the above manner.

In the description described above, the flow of process performed on one slide glass 100 has been described, but four slide glasses 100 are synchronously processed in the sample image capturing device 1. That is, the operation of transporting the slide glass 100 being at the introducing position 60a to the barcode reading position 60b, the operation of transporting the slide glass 100 being at the barcode reading position 60b to the drawing position 60c so that the slide chuck 31 can chuck the slide glass 100, the operation of transporting the slide glass 100 whose images have been captured being at the drawing position 60c to the slide rack storage waiting position 60d, and the operation of storing the slide glass 100 being at the slide rack storage waiting position 60d are synchronously performed. The reading of the barcode, the image capturing of the sample, and storage to the slide rack 300 are synchronously performed at each position of the four slide glasses 100 while the four slide glasses 100 are synchronously transported.

Figure 17:
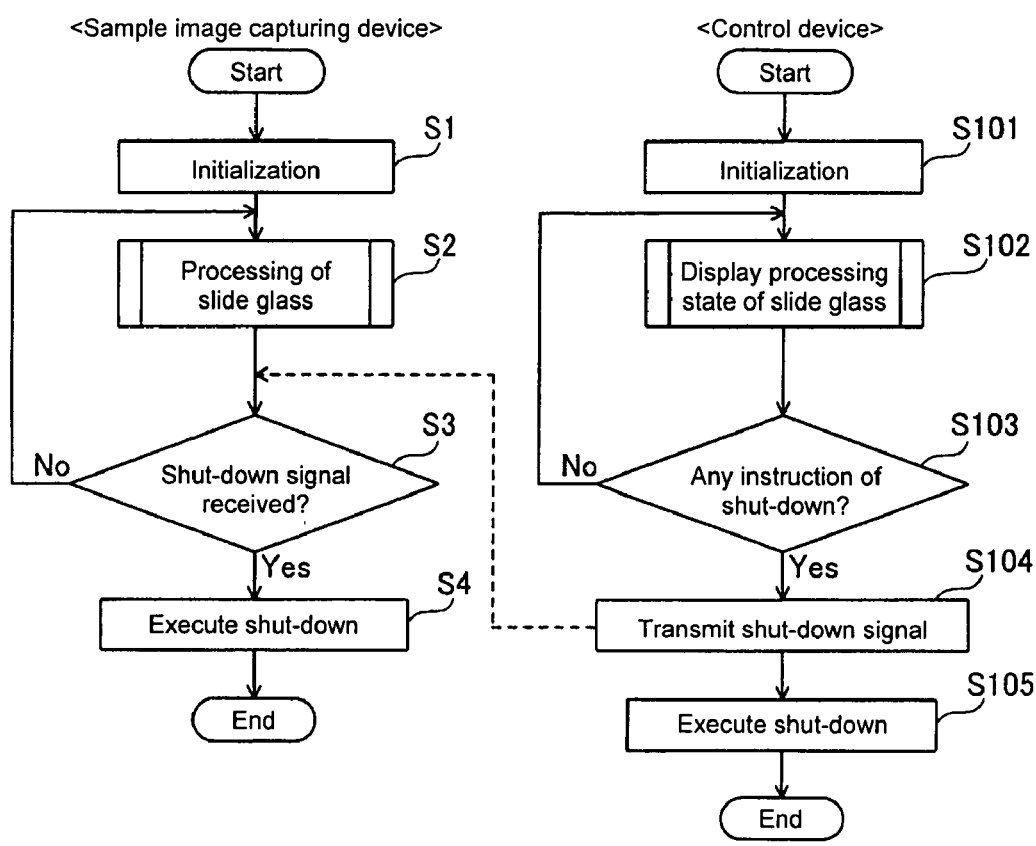
FIG. 17 is a flowchart describing the operation of the automatic blood image analyzer shown in FIG. 1.

FIG. 17 is a flowchart describing the outline of the control of the blood image analyzer configured by the sample image capturing device and the control device according to the present embodiment. The outline of the control of the blood image analyzer 3 configured by the sample image capturing device 1 and the control device 2 will now be described with reference to FIG. 17.

The blood image analyzer 3 is activated when the power of the sample image capturing device 1 and the control device 2 are turned ON. In step S1, initialization is performed in the sample image capturing device 1. Specifically, the movement mechanism 15, the slide chuck 31, and the like are arranged at the initial positions.

In step S2, the process of the slide glass 100 such as image capturing of the sample is performed in the sample image capturing device 1. This process will be hereinafter described in detail.

In step S3, reception of the shut-down signal by the control device 2 is determined in the sample image capturing device 1. If the shut-down signal is not received, the process returns to step S2. If the shut-down signal is received, the shut-down of the sample image capturing device 1 is executed in step S4, and the power of the sample image capturing device 1 is automatically turned OFF. The operation of the blood image analyzer 3 configured by the sample image capturing device 1 and the control device 2 is then terminated.

In step S101, initialization is performed in the control device 2. Specifically, initialization of program etc. stored in the controller 2a is performed. In step S102, the state of process performed in the sample image capturing device 1 is displayed in the control device 2. This display will be hereinafter described in detail.

After the processing of the slide glass 100 is terminated, the user instructs the shut-down with the control device 2. In step S103, whether instruction of shut-down has been made by the user is judged in the control device 2. If the instruction of shut-down is not made, the process returns to step S102. If instruction of shut-down is made, the control device 2 transmits the shut-down signal to the sample image capturing device 1 in step S104, the shut-down of the control device 2 is executed in step S105, and the power of the control device 2 is turned OFF.

FIG. 18 is a flowchart describing the processing operation of the slide glass by the sample image capturing device in step S2 of FIG. 17, and the displaying operation of the processing state of the slide glass by the control device in step S102 of FIG. 17. FIGS. 19 and 20 are views showing a storage table for storing the position of the slide glass and the sequence number assigned to the slide glass in correspondence to each other. The processing operation of the slide glass 100 by the sample image capturing device 1 and the displaying operation of the processing state of the slide glass 100 by the control device 2 will now be described with reference to FIGS. 11, 12, 15, 16, and 18 to 20.

In the sample image capturing device 1, four slide glasses 100 are synchronously transported, and reading of barcode, image capturing of the sample, storage to the slide rack 300, and the like are synchronously performed, as described above. The process when executing the operation of synchronously transporting each of the four slide glasses to the next transportation with the slide glass 100 scheduled to be transported to the barcode reading position 60b being at the introducing position 60a, the slide glass 100 scheduled to be transported to the drawing position 60c for image capturing and gripped by the slide chuck 31 being at the barcode reading position 60b, the slide glass 100 completed with image capturing and scheduled to be transported to the slide rack storage waiting position 60d being at the drawing position 60c, and the slide glass 100 scheduled to be stored in the storing part 300c of the slide rack 300 being at the slide rack storage waiting position 60d. When such synchronous transporting operation is executed, whether or not the first sensor (sensor 61) is turned ON is first judged in step S11 in the sample image capturing device 1. If the first sensor (sensor 61) is turned OFF, the controller 50 judges that the slide glass 100, which should have been transported to the barcode reading position 60b, is not transported to the barcode reading position 60b, thereby recognizing error in the transporting operation and stopping the transporting operation. In step S17, the controller 50 transmits a transportation error signal to the control device 2, and terminates the process. Such process is similarly performed in steps S14, S15, and S16.

If judged that the first sensor (sensor 61) is turned ON in step S11, a sequence number is assigned to the slide glass 100 transported to the barcode reading position 60b in step S12. The sequence number is assigned so that the sequentially transported slide glasses 100 will not be redundant to each other. The controller 50 manages each slide glass 100 by sequence number. As shown in FIG. 19, the sequence number is stored in the storage table by the controller 50, where the position of the slide glass 100 and the sequence number of the slide glass 100 are corresponded to each other. For instance, as shown in FIG. 19, the sequence number "000006" is stored in correspondence to the first sensor (sensor 61) for detecting the slide glass 100 being at the barcode reading position 60b. In FIG. 19, the sequence number "000005" is stored in correspondence to the second sensor (sensors 39a to 39c. for checking whether or not the slide glass 100 is chucked by the slide chuck 31) for detecting the slide glass 100 being at the image capturing position. The sequence number "000004" is stored in correspondence to the third sensor (sensor 62) for detecting the slide glass 100 being at the slide rack storage waiting position 60d. The sequence number "000003" is stored in correspondence to the fourth sensor (sensor 45) for detecting the storage of the slide glass 100 in the slide rack 300. The sequence number "000002" is stored in correspondence to the first storing part (storing part 300c positioned at the top of the slide rack 300), and the sequence number "000001" is stored in correspondence to the second storing part (storing part 300c positioned second from the top of the slide rack 300).

In step S13, the two-dimensional barcode of the slide glass 100 transported to the barcode reading position 60b is read in the sample image capturing device 1. The content (ID) of the read barcode is stored in the controller 50 in correspondence to the sequence number. If the reading of the barcode fails, the controller 50 assigns an error number instead of the ID in correspondence to the sequence number of the slide glass 100 which reading has failed.

In step S14, whether or not the second sensor (sensors 39a to 39c) is turned ON (whether or not the slide glass 100 is chucked by the slide chuck 31) is judged in the sample image capturing device 1 (see FIGS. 11 and 12). If the second sensor is turned OFF (if the slide glass 100 is not chucked by the slide chuck 31), the controller 50 judges that the slide glass 100, which should have been transported to the image capturing position through the drawing position 60c from the barcode reading position 60b, is not transported to the image capturing position, thereby recognizing error in the transporting operation and stopping the transporting operation. In step S17, the controller 50 transmits a transportation error signal to the control device 2.

If judged that the second sensor is turned ON in step S14, whether or not the third sensor (sensor 62) is turned ON is judged in step S15. If the third sensor is turned OFF, the controller 50 judges that the slide glass 100, which should have been transported to the slide rack storage waiting position 60d through the drawing position 60c from the image capturing position, is not transported to the slide rack storage waiting position 60d, thereby recognizing error in the transporting operation and stopping the transporting operation. In step S17, the controller 50 transmits a transportation error signal to the control device 2.

If judged that the third sensor is turned ON in step S15, whether or not the fourth sensor (sensor 45) is turned ON is judged in step S16. If the fourth sensor is turned OFF, the controller 50 judges that the slide glass 100, which should have been transported to the storing part 300c of the slide rack 300 from the slide rack storage waiting position 60d, is not stored in the storing part 300c, thereby recognizing error in the transporting operation and stopping the transporting operation. In step S17, the controller 50 transmits a transportation error signal to the control device 2. If judged that the fourth sensor is turned ON in step S16, the controller 50 judges that the transporting operation has been correctly performed, and proceeds to step S18.

Although not shown, when the slide glass 100 is not continuously supplied to the introducing position 60a, and the slide glass 100 to be transported to the barcode reading position 60b in the next transporting operation is not at the introducing position 60a, the judgment of step S11 is not performed and the process proceeds to step S14 in the processing flow of FIG. 18 performed immediately after the execution of the transporting operation. When the slide glass 100 to be transported to the drawing position 60c in the next transporting operation is not at the barcode reading position 60b, the judgment of step S14 is not performed and the process proceeds to step S15 in the processing flow of FIG. 18 performed immediately after the execution of the transporting operation. Furthermore, when the slide glass 100 to be transported to the slide rack storage waiting position 60d in the next transporting operation is not at the drawing position 60c, the judgment of step S15 is not performed and the process proceeds to step S16 in the processing flow of FIG. 18 performed immediately after the execution of the transporting operation. Moreover, when the slide glass 100 to be stored in the storing part 300c of the slide rack 300 in the next transporting operation is not at the slide rack storage waiting position 60d, the judgment of step S16 is not performed and the process proceeds to step S18 in the processing flow of FIG. 18 performed immediately after the execution of the transporting operation.

In step S18, the controller 50 transmits the data (correspondence relationship of position of slide glass 100, sequence number, and ID) stored in the storage table (see FIG. 19) to the control device 2 in the sample image capturing device 1. The data (correspondence relationship of position of slide glass 100, sequence number, and error number) is transmitted for the slide glass 100 which barcode reading has failed.

In step S19, whether or not order information is received from the control device 2 is judged in the sample image capturing device 1. The order information is information such as image capturing condition necessary for the image capturing unit 30 to perform image capturing of the slide glass 100. If the order information is not received, such judgment is repeated. If the order information is received, image capturing of the sample positioned at the image capturing position is performed based on the received order information in step S20. In step S21, the data of the captured image (captured image data) obtained in the image capturing unit 30 is transmitted to the control device 2.

In step S22, the slide glass 100 is transported in the sample image capturing device 1. In other words, the operation of transporting the slide glass 100 being at the introducing position 60a to the barcode reading position 60b, the operation of transporting the slide glass 100 being at the barcode reading position 60b through the drawing position 60c to the image capturing position, the operation of transporting the slide glass 100 whose images have been captured being at the image capturing position to the slide rack storage waiting position 60d through the drawing position 60c, and the operation of storing the slide glass 100 being at the slide rack storage waiting position 60d in the slide rack 300 are synchronously performed.

Subsequently, in step S23, the storage table stored in the controller 50 is updated in correspondence to the arrangement of the slide glass 100 after transportation in step S22. That is, the sequence number of the storage table shown in FIG. 19 is shifted one level at a time to update to the state shown in FIG. 20, and the process returns. If shut-down is not performed thereafter (see FIG. 17), the process of step S2 is performed, and the process of the slide glass 100 by the sample image capturing device 1 is continued.

In step S111, whether or not the transportation error signal is received from the controller 50 is judged in the control device 2. If the transportation error signal is received, transportation error is displayed on the display 2b in step S112, and the display of the processing state of the control device 2 is terminated.

In step S113, whether or not data is received is judged in the control device 2. If data is not received, such judgment is repeated. If data is received, order information is created in step S114. In step S115, the created order information is transmitted to the controller 50 of the sample image capturing device 1.

In step S116, the control device 2 displays each ID corresponding to the slide glass 100 positioned at each position (barcode reading position, image capturing position, etc.) on the first ID display region 211, the second ID display region 212, the third ID display region 215, and the fourth ID display region 216 of the analyzing state screen 210 shown in FIG. 15 based on the data (storage table) received in step S113. The error number ("ERRO . . . 01" shown in FIG. 15) is displayed instead of the ID for the slide glass 100 which barcode reading has failed.

In step S117, whether or not the captured image data is received from the sample image capturing device 1 is judged in the control device 2. If the captured image data is not received, such judgment is repeated. If the captured image data is received, the captured image is displayed on the image display region 213 of the analyzing state screen 210 of the display 2b. In step S119, analysis (categorization of blood cells) is performed based on the captured image data in the control device 2. In step S120, the analysis result of analysis in step S119 is displayed on the analysis result display region 214 of the analyzing state screen 210 of the display 2b, and the process returns. Thereafter, if the shut-down is not performed (see FIG. 17) in the control device 2, the process of step S102 is performed every time the slide glass 100 is transported in the sample image capturing device 1.

In the blood image analyzer 3, after one round of processes of steps S11 to S23 and steps S111 to S120 is terminated, the analyzing state screen 210 shown in FIG. 15 changes to the analyzing state screen 210 shown in FIG. 16. When the four slide glasses 100 are synchronously transported by one transporting operation, the ID or the error number displayed on the first ID display region 211, the second ID display region 212, and the third ID display region 215 in FIG. 15 are synchronously moved to and displayed on the second ID display region 212, the third ID display ID region 215, and the fourth ID display region 216, as shown in FIG. 16. In FIG. 16, ID of the slide glass 100 from which the barcode is newly read is displayed on the first ID display region 211. Therefore, ID of the four slide glasses 100 in the sample image capturing device 1 are displayed in real time in association with the position of the slide glass 100 on the display 2b of the control device 2 in accordance with the transporting state of the slide glass 100 in the sample image capturing device 1.

In the present embodiment, ID of the slide glass 100 positioned at each of the barcode reading position 60b, the image capturing position, the slide rack storage waiting position 60d, and the slide rack 300 are each displayed on the first ID display region 211, the second ID display region 212, the third ID display region 215, and the fourth ID display region 216 of the analyzing state screen 210 based on the detection result of the sensors 39a to 39c, 45, 61, and 62, as described above. If the apparatus stops by error and the like, the user checks the ID displayed in association with each position in the analyzing state screen 210 to recognize the ID of the slide glass 100 positioned at each position. The target slide glass 100 can be immediately searched in the stopped apparatus. Therefore, even if the apparatus is stopped, the user can rapidly respond to the predetermined slide glass 100 in process in the apparatus.

In the present embodiment, the arrangement in the analyzing state screen 210 of the first ID display region 211, the second ID display region 212, the third ID display region 215, and the fourth ID display region 216 on which each ID of the fourth slide glasses 100 positioned at each of the barcode reading position 60b, the image capturing position, the slide rack storage waiting position 60d, and the slide rack 300 are displayed are each corresponded to the planar arrangement of each position in the sample image capturing device 1, as described above, so that the user can easily recognize at which position the target slide glass 100 is positioned on the analyzing state screen 210.

In the present embodiment, an indication of "Slide ID waiting for measurement" is adjacent to the first ID display region 211, as shown in FIGS. 15 and 16. Therefore, the user can easily recognize that the first ID display region 211 shows the ID of the slide glass 100 which is to be measured/analyzed. Furthermore, the user can easily recognize that the slide glass 100 whose ID is displayed in the first ID display region 211 is positioned at the barcode reading position 60b.

Likewise, an indication of "Slide ID in measurement" is adjacent to the second ID display region 212, as shown in FIGS. 15 and 16. Therefore, the user can easily recognize that the second ID display region 212 shows the ID of the slide glass 100 which is in measurement/analysis. Furthermore, the user can easily recognize that the slide glass 100 whose ID is displayed in the second ID display region 212 is positioned at the image capturing position.

Likewise, an indication of "Slide ID waiting to be stored" is adjacent to the third ID display region 215, as shown in FIGS. 15 and 16. Therefore, the user can easily recognize that the third ID display region 215 shows the ID of the slide glass 100 which has been measured/analyzed and is waiting to be stored in the slide rack 300. Furthermore, the user can easily recognize that the slide glass 100 whose ID is displayed in the third ID display region 215 is positioned at the slide rack storage waiting position 60d.

Likewise, an indication of "Storage information" is adjacent to the fourth ID display region 216, as shown in FIGS. 15 and 16. Therefore, the user can easily recognize that the fourth ID display region 216 shows the ID of the slide glass 100 which is stored in the slide rack 300. Furthermore, the user can easily recognize that the slide glass 100 whose ID is displayed in the fourth ID display region 215 is positioned at the slide rack 300.

In the present embodiment, the user can easily recognize in which storing part 300c of the slide rack 300 the target slide glass 100 is stored in the analyzing state screen 210 by corresponding the arrangement in the fourth ID display region 216 of each ID of the plurality of slide glasses 100 stored in the slide rack 300 with the arrangement in the slide rack 300 of the storing part 300c in which each slide glass 100 is stored, as described above.

In the present embodiment, if acquisition of the ID of the slide glass 100 by the barcode reader 20 fails, the user can recognize at which position the slide glass 100 which acquisition of ID failed is positioned in the analyzing state screen 210 by displaying the error number on the first ID display region 211, the second ID display region 212, the third ID display region 215, and the fourth ID display region 216 of the analyzing state screen 210 in place of the ID, as described above.

In the present embodiment, the blood image analyzer 3 includes the first sensor 61 for detecting the slide glass 100 being at the reading position 60b of the barcode reader 20 of the sample image capturing device, and second sensors 39a, 39b and 39c for detecting the slide glass 100 being at the image capturing position of the image capturing unit 30. In such configuration, the analyzing state screen 210 includes the image display region 213 for displaying the captured image of the sample. The controller 2a acquires the captured image data of the sample during image capturing of the image capturing unit 3 at the image capturing position. The controller 2a controls the display 2b to display the captured image of the sample acquired from the image capturing unit 30 on the image display region 213. According to such configuration, the user can visually check the captured image of the slide glass 100 being image captured on the analyzing state screen 210.

In particular, the image capturing unit 30 sequentially captures the plurality of blood images from one slide glass 100 at the image capturing position. The controller 2a is configured to acquire the captured blood image of the slide glass 100 at the image capturing position in real time while the image capturing unit 30 is sequentially capturing a plurality of blood images from one slide glass 100 at the image capturing position. Furthermore, the controller 2a controls the display so as to display the blood image acquired in real time on the captured image display region while the image capturing unit 30 is sequentially capturing a plurality of blood images from one slide glass 100 at the image capturing position. According to such configuration, the user can visually check in real time the captured image of the slide glass 100 being captured on the analyzing state screen 210.

Moreover, in the present embodiment, the controller 2a acquires the captured image data of the sample during image capturing by the image capturing unit 30 at the image capturing position. The controller 2a analyzes the sample based on the captured image data, and controls the display 2b to display the analysis result of the sample on the analysis result display region 214. According to such configuration, the user can check the analysis result of images of the sample being captured on the analyzing state screen 210.

In particular, the controller 2a analyzes the blood image acquired in real time while the image capturing unit 30 is sequentially capturing a plurality of blood images from one slide glass 100 at the image capturing position. According to such configuration, the user can visually check in real time the captured image of the slide glass 100 being captured on the analyzing state screen 210.

The embodiment disclosed herein should be considered as illustrative and not restrictive in various aspects. The scope of the present invention is as defined by the appended claims and not by the description of the embodiment, and all meanings equivalent to the claims and modifications made within the scope should be recognized as being enclosed therein.

For instance, in the embodiment, a configuration of moving the slide glass 100 from the introducing position 60a to the barcode reading position 60b, the drawing position 60c, the slide rack storage waiting position 60d, and into the slide rack 300 by means of one transportation part consisting of the slide transportation mechanism 10 arranged along the pathway 60 has been described by way of example, but the present invention is not limited thereto, and two transportation parts of a transportation part for transporting the slide glass from the introducing position to the drawing position and a transportation part for transporting the slide glass from the drawing position to the slide rack storage waiting position and into the slide rack may be arranged.

Furthermore, an example of performing transportation error display on the display 2b when error is found in the transporting operation has been described in the embodiment, but the present invention is not limited thereto, and the transportation error display may be individually performed on the first ID display region 211, the second ID display region 212, the third ID display region 215, and the fourth ID display region 216. For instance, if the slide glass 100 does not reach the barcode reading position 60b and transportation error is made, the transportation error display may be performed on the first ID display region 211 corresponding to the barcode reading position 60b. According to such configuration, the user can recognize to which position the slide glass 100 was not transported that caused the transportation error on the analyzing state screen 210.

An example of displaying the ID of the slide glass 100 positioned at each of the four positions in the sample image capturing device 1 on the analyzing state screen 210 has been described in the above embodiment, but the present invention is not limited thereto, and the ID of the slide glass 100 positioned at each of five or more positions or three or less positions may be displayed.

The foregoing detailed description and examples have been provided by way of explanation and illustration, and are not intended to limit the scope of the appended claims. Many variations in the presently desirable embodiments illustrated herein will be obvious to one of ordinary skill in the art, and remain within the scope of the appended claims and their equivalents.

What is claimed is:

1. A blood image analyzer for analyzing a blood image comprising:
    an image capturing unit for capturing a blood image of a sample;
    an analyzing part for analyzing the sample based on the blood image captured by the image capturing unit;
    an identification information reader for reading, from the sample, identification information assigned to the sample;
    a transportation part for transporting the sample to the identification information reader and the image capturing unit;
    a first detector for detecting the sample at a first detection position on a pathway of the sample transported by the transportation part;

a second detector for detecting the sample at a second detection position on the pathway;

a display; and a controller for controlling the display, so as to display, based on detection results by the first detector and the second detector, a screen including a first identification information display region and a second identification information display region, wherein the first identification information display region displays identification information of the sample being at the first detection position; and the second identification information display region displays identification information of the sample being at the second detection position.

2. The blood image analyzer according to claim 1, wherein the first identification information display region and the second identification information display region are displayed on the screen so as to reflect positional relationship of the first detection position and the second detection position on the pathway.

3. The blood image analyzer according to claim 2, wherein positional relationship between the first detection position and the second detection position is a planar positional relationship.

4. The blood image analyzer according to claim 1, wherein the first detection position is an identification information reading position where identification information of the sample is read by the identification information reader; and the second detection position is an image capturing position where the image of the sample is captured by the image capturing unit.

5. The blood image analyzer according to claim 1, further comprising a third detector for detecting the sample at a third detection position on the pathway; wherein the screen includes a third identification information display region; and the controller controls the display, so as to display, based on a detection result by the third detector, identification information of the sample being at the third detection position in the third identification information display region.

6. The blood image analyzer according to claim 5, further comprising a storing part setting unit in which a storing part for storing the sample is set after the image of the sample is captured by the image capturing unit, wherein the third detection position is a storage position where the sample is stored in the storing part set in the storing part setting unit.

7. The blood image analyzer according to claim 6, wherein the storing part is configured to store a plurality of samples.

8. The blood image analyzer according to claim 7, wherein the controller controls the display so as to display each identification information of the plurality of samples stored in the storing part in the third identification information display region.

9. The blood image analyzer according to claim 8, wherein the controller controls the display so as to display each identification information of the plurality of samples stored in the storing part in the third identification information display region in correspondence to arrangement of the plurality of samples in the storing part.

10. The blood image analyzer according to claim 5, further comprising a fourth detector for detecting the sample at a fourth detection position on the pathway; wherein the screen includes a fourth identification information display region; and the controller controls the display, so as to display, based on a detection result by the fourth detector, identification information of the sample being at the fourth detection position in the fourth identification information display region.

11. The blood image analyzer according to claim 10, wherein the transportation part is configured to have the sample wait at a storage waiting position near the storing part to store the sample in the storing part; and the fourth detection position is the storage waiting position.

12. The blood image analyzer according to claim 1, wherein the screen includes a captured image display region for displaying the blood image.

13. The blood image analyzer according to claim 12, wherein .

the image capturing unit sequentially captures a plurality of blood images from the sample at the image capturing position;

the controller sequentially acquires the plurality of blood images captured by the image capturing unit; and the controller controls the display so as to display the acquired blood images in the captured image display region.

14. The blood image analyzer according to claim 13, wherein the controller acquires in real time captured blood images of the sample at the image capturing position, while the image capturing unit is sequentially capturing the plurality of blood images from the sample at the image capturing position, and the controller controls the display so as to display the blood images acquired in real time in the captured image display region while the image capturing unit is sequentially capturing the plurality of blood images from the sample at the image capturing position.

15. The blood image analyzer according to claim 1, wherein the screen includes an analysis result display region for displaying result of analysis of the sample by the analyzing part;

the image capturing unit sequentially captures a plurality of blood images from the sample at the image capturing position;

the controller sequentially acquires the plurality of blood images captured by the image capturing unit;

the analyzing part sequentially analyzes the blood images acquired by the controller; and the controller controls the display so as to display the result of analysis by the analyzing part on the analysis result display region.

16. The blood image analyzer according to claim 1, wherein the controller controls the display so as to display, when reading of identification information of the sample by the identification information reader fails, reading error information indicating that reading of the identification information has failed in the first identification information display region of the screen.

17. The blood image analyzer according to claim 1, wherein the controller detects that the sample has not reached the first detection position based on the detection result of the first detector.

18. The blood image analyzer according to claim 17, wherein the controller controls the display so as to display sample non-arrival information indicating that the sample has not reached the first detection position in the first identification information display region of the screen when detecting that the sample has not reached the first detection position.

19. The blood image analyzer according to claim 17, wherein the controller detects that the sample has not reached the first detection position based on the detection result of the first detector and information relating to a timing the sample is to reach the first detection position.

20. The blood image analyzer according to claim 1, wherein:
the sample is a blood smear prepared on a slide glass;
the slide glass comprises a sample information display region stored with identification information; and
the identification information reader reads identification information from the sample information display region.

21. The blood image analyzer according to claim 1, wherein:
the first identification information display region displays location information regarding the first detection position; and
the second identification information display region displays location information regarding the second detection position.

22. A blood image analyzer for analyzing a blood image comprising:
an image capturing unit for capturing a blood image of a sample;
an analyzing part for analyzing the sample based on the blood image captured by the image capturing unit;
a storing part setting unit for setting a storing part for storing the sample whose image has been captured by the image capturing unit,
a first transportation part for transporting the sample to a relay position;
a second transportation part for transporting the sample from the relay position to an image capturing region where image is captured by the image capturing unit, and transporting the sample from the image capturing region to the relay position;
a third transportation part for transporting the sample whose image has been captured by the image capturing unit from the relay position to the storing part set in the storing part setting unit;
first, second, and third sample detectors for detecting the sample at the first transportation part, the second transportation part, and the third transportation part;
a display; and
a controller for controlling the display, based on detection results of the first, second, and third sample detectors, so as to display a screen including sample position display region for displaying that the sample is positioned at one of a pathway of the first transportation part, a pathway of the second transportation part, or a pathway of the third transportation part.

23. A blood image analyzer for analyzing a blood image comprising:
an image capturing unit for capturing a blood image of a sample;
an analyzing part for analyzing the blood image;
a transportation part for transporting the sample along a pathway to/from the image capturing unit;
a first detector for detecting the sample at a first detection position on the pathway;
a second detector for detecting the sample at a second detection position on the pathway;
a display; and
a controller for controlling the display, so as to display, based on detection results by the first detector and the second detector, a screen including a first location information display region and a second location information display region, wherein
the first location information display region displays information regarding the location of the sample being at the first detection position; and
the second location information display region displays information regarding the location of the sample being at the second detection position.

* * * * *